United States Patent
Kopperschmidt et al.

(10) Patent No.: US 11,744,959 B2
(45) Date of Patent: Sep. 5, 2023

(54) GRIPPER APPARATUS FOR CANNULAS

(71) Applicant: FRESENIUS MEDICAL CARE DEUTSCHLAND GMBH, Bad Homburg (DE)

(72) Inventors: Pascal Kopperschmidt, Dittelbrunn (DE); Pia Daniel, Bodman (DE); Reiner Spickermann, Wasserlosen-Burghausen (DE); Otto Arkossy, Budapest (HU); Cacilia Scholz, Schwalbach (DE); Kai-Uwe Ritter, Rednitz-Hembach (DE); Elke Schulte, Schweinfurt (DE); Christopher Hauke, Mainz-Kostheim (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 1078 days.

(21) Appl. No.: 16/479,941

(22) PCT Filed: Jan. 29, 2018

(86) PCT No.: PCT/EP2018/052116
§ 371 (c)(1),
(2) Date: Jul. 23, 2019

(87) PCT Pub. No.: WO2018/138326
PCT Pub. Date: Aug. 2, 2018

(65) Prior Publication Data
US 2019/0336705 A1 Nov. 7, 2019

(30) Foreign Application Priority Data
Jan. 30, 2017 (DE) ...................... 10 2017 201 451.2

(51) Int. Cl.
*A61M 5/32* (2006.01)
*A61B 34/30* (2016.01)
(Continued)

(52) U.S. Cl.
CPC ....... *A61M 5/3287* (2013.01); *A61B 17/3403* (2013.01); *A61B 34/30* (2016.02);
(Continued)

(58) Field of Classification Search
CPC .. A61M 5/3287; A61M 5/3204; A61M 5/343; A61M 5/3293; A61M 5/3205;
(Continued)

(56) References Cited

U.S. PATENT DOCUMENTS

| | | | |
|---|---|---|---|
| 5,201,716 A | 4/1993 | Richard | |
| 5,647,373 A | 7/1997 | Paltieli | |

(Continued)

FOREIGN PATENT DOCUMENTS

| | | |
|---|---|---|
| CN | 104856649 A | 8/2015 |
| JP | 2000086144 A | 3/2000 |

(Continued)

OTHER PUBLICATIONS

International Preliminary Report on Patentability issued in corresponding International Patent Application No. PCT/EP2018/052116 dated Aug. 8, 2019 (11 pages).

(Continued)

*Primary Examiner* — Nathan R Price
*Assistant Examiner* — Anh Bui
(74) *Attorney, Agent, or Firm* — Kilyk & Bowersox, P.L.L.C.

(57) ABSTRACT

The invention relates to a gripper apparatus for a cannulation robot and for gripping a cannula having a cannula holder. The gripper apparatus comprises two gripper elements and a moving device. The two gripper elements can be moved (Continued)

relative to each other and work in concert to grip the cannula holder. The moving device is designed to move the two gripper elements relative to each other and at least one of the gripper elements relative to the cannula holder. The gripper apparatus can thereby be brought into a gripping state, in which at least one of the gripper elements is engaged with the cannula holder, by means of the moving device.

10 Claims, 10 Drawing Sheets

(51) Int. Cl.
  *A61B 17/34* (2006.01)
  *A61B 34/00* (2016.01)
  *A61M 25/01* (2006.01)
  *A61M 25/02* (2006.01)

(52) U.S. Cl.
  CPC ........... *A61B 34/70* (2016.02); *A61M 25/013* (2013.01); *A61B 2017/3409* (2013.01); *A61M 5/3204* (2013.01); *A61M 25/02* (2013.01)

(58) Field of Classification Search
  CPC ................ A61M 25/013; A61M 25/02; A61M 2005/206; A61M 2005/3206; A61B 17/3403; A61B 34/30; A61B 34/70; A61B 2017/3409
  See application file for complete search history.

(56) References Cited

U.S. PATENT DOCUMENTS

| | | |
|---|---|---|
| 2003/0060716 A1 | 3/2003 | Heidrich |
| 2006/0161136 A1 | 7/2006 | Anderson et al. |
| 2013/0242082 A1* | 9/2013 | Miller .................. G06T 7/0004 |
| | | 348/94 |
| 2015/0065916 A1 | 3/2015 | Maguire et al. |
| 2015/0210410 A1 | 7/2015 | Umeno et al. |
| 2016/0249990 A1 | 9/2016 | Glozman et al. |
| 2016/0346060 A1 | 12/2016 | Nawrat et al. |
| 2017/0086930 A1 | 3/2017 | Thompson et al. |

FOREIGN PATENT DOCUMENTS

| | | |
|---|---|---|
| JP | 2000356642 A | 12/2000 |
| JP | 2001001288 A | 1/2001 |
| JP | 2016120313 A | 7/2016 |
| WO | 2012088471 A1 | 6/2012 |

OTHER PUBLICATIONS

Decision of Rejection issued in corresponding Chinese Patent Application 201880009321.4 dated Apr. 1, 2022 (English translation only)(13 pages).

International Search Report and Written Opinion issued in corresponding International Patent Application No. PCT/EP2018/052116 (with English translation of International Search Report) dated May 2, 2018 (17 pages).

* cited by examiner

Fig. 10
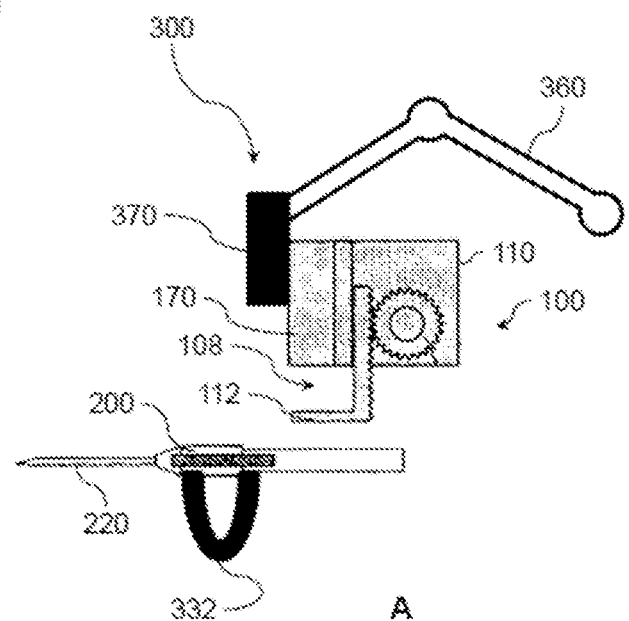
A
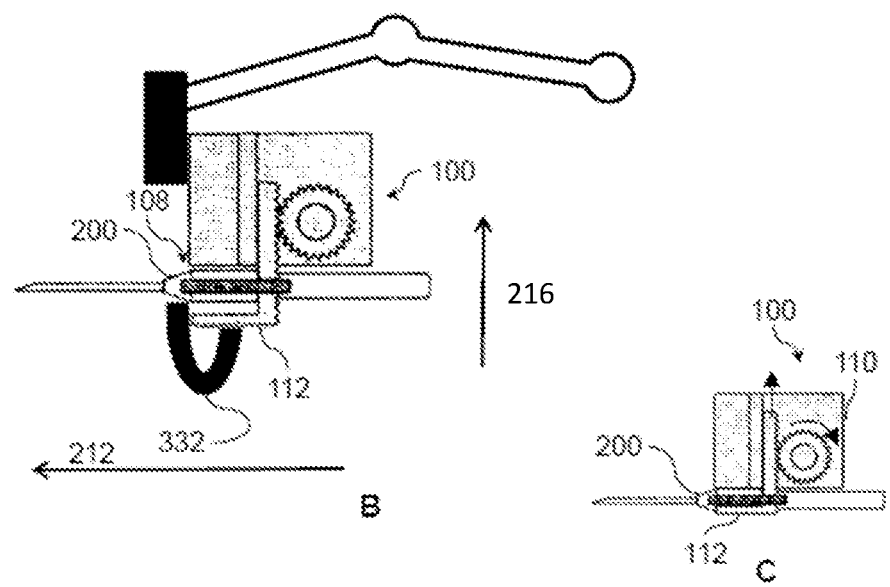
B
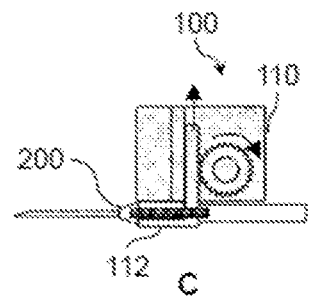
C

GRIPPER APPARATUS FOR CANNULAS

This application is a National Stage Application of PCT/EP2018/052116, filed Jan. 29, 2018, which claims priority to German Patent Application No. 10 2017 201 451.2, filed Jan. 30, 2017.

The present invention relates to the field of medical technology and in particular to a gripper apparatus for a cannulation robot for gripping a cannula, a cannulation robot and a method for the automated gripping of a cannula.

The puncturing of blood vessels, also known as cannulation, is a routine procedural step in the medical treatment of many patients in which a fluid connection is established between a patient's blood circulation and an external fluid system, in particular a cannula. Cannulation is usually performed by physicians or trained personnel. The quality of the vascular access created by the cannulation thereby depends on a plurality of parameters which are in particular affected by the individual and temporally varying abilities of the medical personnel and the physical characteristics of the patients to be treated as well as the diversity of the technical instruments used in the cannulation. In order to standardize cannulation, auxiliary apparatus have been developed to support the medical personnel during cannulation. For example, an apparatus for inserting the distal end of a cannula into a vessel is known from EP 1 244 491 B1.

Cannulation, being a routine procedural step in many treatments, is also frequently performed. In order to thereby standardize cannulation, make efficient use of financial as well as personnel resources, and reliably ensure high treatment quality, cannulation robots have been developed which autonomously perform a cannulation procedure on patients using suitable sensor technology and motor function. Such cannulation robots and the technical resources thereby used are known from e.g. EP 0 654 244 B1, US 2015/0065916 A1 and WO 2015/052719 A1.

The observations of the use of cannula and the development of cannulation robots and auxiliary apparatus for cannulation which underlie the present invention revealed that when a cannula is handled, in particular grasped, mistakes can occur, the cannula can become contaminated and/or the assistance or intervention of medical staff can be necessary. The gripping of a cannula thereby affects the treatment quality and/or the resource efficiency, particularly in the case of automated cannulation.

The invention is based on the task of, in particular for the further automating of cannulation, automating the gripping of the cannula, increasing cannula gripping reliability and/or improving the hygienics.

The invention respectively solves this task by a gripper apparatus in accordance with the teaching of independent claim 1, a cannula holder in accordance with the teaching of independent claim 13, a cannulation robot in accordance with the teaching of independent claim 14, and a method for the automated gripping of a cannula according to the teaching of independent claim 15. Preferential embodiments, further developments or variants in particular constitute the subject matter of the independent claims. The subject matter of the claims is expressly made a part of the specification disclosure.

A first aspect of the invention relates to a gripper apparatus for a cannulation robot and for gripping a cannula with a cannula holder. The gripper apparatus comprises two gripper elements and a moving device. The two gripper elements are movable relative to each other and work in concert to grip the cannula holder. The moving device is configured to move the two gripper elements relative to each other and to move at least one of the gripper elements relative to the cannula holder. The moving device can thereby bring the gripper apparatus into a gripping state for gripping in which at least one of the gripper elements engages with the cannula holder.

In the sense of the invention, a "gripper apparatus" is at least to be understood as an apparatus designed to mechanically grasp an object. In particular, the gripper apparatus can realize a gripping action; i.e. grabbing the object, and thereby make an indirect or direct mechanical connection with the object. Preferably, the connection is disengageable, the grasped object can thus be released.

In the sense of the invention, a "cannula" is a tubular body, in particular a rigid or flexible injection needle, with a lumen having a geometry and external dimensions suitable for use in the cannulation of a blood vessel. Preferably, the cannula comprises a hollow needle and a connector part. The connector part can in particular be arranged at the proximal end of the cannula and connected, in particular integrally, to the hollow needle so that the cannula can be connected at its proximal end in form-fit or force-fit manner to further apparatus, in particular an infusion tube or a medical syringe, in particular pushed onto same, and the lumen of the cannula can be fluidly connected to the further apparatus. Preferably, the hollow needle at the distal end of the cannula provided for introduction into a blood vessel is sharp-tipped—in particular with a pointed bevel cut—or blunt. Preferably, the hollow needle is made from metal and/or the connector part made from plastic. Preferentially, the cannula can also comprise a cannula holder, wherein the cannula, in particular the hollow needle and/or the connector part, can be form-fit or force-fit connected to or preferably integrally connected to the cannula holder.

In the sense of the invention, a "cannula holder" is at least to be understood as an apparatus by means of which a mechanical connection can be made between a cannula and a gripper apparatus. In particular, a cannula holder is designed to be mechanically connected, in particular integrally, to a cannula on one side and mechanically connected, preferably detachably, to the gripper apparatus on the other side.

One advantage of the gripper apparatus can in particular be the cannula being grasped by means of the cannula holder, whereby, particularly compared to a commercial cannula without cannula holder, the respective cannula and/or gripper apparatus is able to be adapted. At least one of the gripper elements is thereby in engagement with the cannula holder, whereby the mechanical stability of the cannula connection to the gripping device and thus the reliability can be increased. This also advantageously enables the cannula holder to be formed and the movement of the two gripper elements to be synchronized to the cannula holder so as to enable automated gripping or thereby increase the reliability. Also an advantage of gripping by means of the cannula holder can in particular be the gripper apparatus not grabbing the cannula or the other cannula component parts—other than the cannula holder—and thus reducing the risk of possible contamination of the gripping device and/or the cannula, whereby in particular the hygienics can be improved.

The following in particular describes preferential further developments of the gripper apparatus and its components, each of which can be respectively combined, insofar as technically feasible and not explicitly excluded, at the option of one skilled in the art. Correspondingly, the preferential further developments can in particular also be combined with preferential embodiments or example embodiments.

According to one preferential further development, the gripper elements, which are engaged with the cannula holder, each comprise a respective grip region which is formed as a counterpart to a region of the cannula holder corresponding thereto. One advantage of the grip region formed as a counterpart can in particular be in its enabling a form-fitting connection to the corresponding region of the cannula holder and thus a reliable mechanical connection in the gripping state.

According to one preferential further development, at least one and preferably all of the grip regions are of a permanent form. These grip regions are thereby arranged at predetermined positions of the cannula holder. This advantageously enables ensuring that the cannula is disposed in a position relative to the gripper elements which is predetermined by means of said grip region during gripping, and particularly when in the gripping state.

According to one preferential further development, one or more, preferably all of the permanently formed grip regions exhibit a centering geometry which cooperates with the corresponding regions such that the respective corresponding region is centered relative to the respective grip region during gripping. Preferably, the centering geometry exhibits or consists of one or more beveled surfaces. The corresponding regions of the cannula holder can accordingly also exhibit beveled surfaces. During gripping, the grip regions with centering geometry and the corresponding regions of the cannula holder can thereby advantageously slide alongside one another along the beveled surfaces until being centered with one another. One advantage of centering geometry can in particular lie in enabling the reconciling of deviations in the initial position of the cannula, in particular the cannula holder, relative to the gripper apparatus, in particular the gripper elements, and/or increasing the precision of the positioning of the cannula in the gripping state, whereby in particular the reliability of the automated gripping and/or, by virtue of the precise positioning, the quality of the treatment, can be increased.

According to one preferential further development, at least in the gripping state and preferably during gripping, the gripper apparatus is at least substantially arranged in an upper area above an upper side of the cannula and/or the grip regions are arranged and the gripper elements formed such that a lower area below the underside of the cannula is kept at least substantially free.

To be understood by the upper side of the cannula is, in terms of cannula partitioning, that side of the cannula along a plane in which a longitudinal axis of the cannula faces away from the patient when the distal end of the cannula is inserted into the patient; i.e. in particular during or after cannulation. Correspondingly, the other side; i.e. the side facing the patient, is the underside of the cannula.

Preferably, the grip regions are arranged and the gripper elements formed such that in the gripping state, the gripper elements project into the lower area at the most 2 cm, preferably at the most 1 cm, preferably at the most 0.5 cm, and further preferentially no more than 1 mm beyond the cannula holder.

One advantage of keeping the lower area, which faces the patient during cannulation, at least substantially free, thus in particular the limited projection into the lower area, can in particular be in being able to use the lower area for orienting and positioning the cannula and/or the angle attainable between the patient and the cannula being at least not substantially limited by parts of the gripper apparatus projecting into the lower area. In particular, this advantageously enables ensuring a flat angle for the insertion or subsequent positioning of the cannula, increasing treatment quality and/or patient comfort.

Preferably, one or more of the grip regions and/or the corresponding regions of the cannula holder determine a rotational position of the cannula with respect to a cannula rotation about a longitudinal axis of said cannula. This advantageously enables the cannula to be brought into a specific rotational position in a manner predetermined by means of the grip regions and the cannula thus oriented relative to a patient in terms of its longitudinal axis, whereby in particular the commonly beveled tip at the distal end of the cannula can be rotated such that the rotational position is particularly suited to the respective cannulation. In particular, the cannula; i.e. in particular its hollow needle, can thereby be beveled in the direction of the cannula's upper side so that the cutting edge of the cannula lies at the underside of the cannula and is oriented toward the patient.

According to one preferential further development, the gripper apparatus only contacts the cannula at or by means of the cannula holder, at least in the gripping state. This advantageously enables increasing the hygienics and thus treatment safety.

To improve in particular the hygienics, the cannula holder is arranged at the proximal end of the cannula according to one preferential further development.

According to one preferential further development for a cannula having a cannula holder arranged at the proximal end, when the gripper elements are gripping, the moving device only moves in the area surrounding the cannula holder and/or the gripper elements are arranged and the moving device moves the gripper elements when gripping such that the surrounding area of the cannula's distal end remains free of the gripper elements. Preferably, the area surrounding the distal end thereby extends at least 5 mm around said distal end, further preferentially 15 mm and/or preferentially at least one-third of the length of the cannula and further preferentially at least half the length of the cannula. Also preferably, the surrounding area of the proximal end thereby extends at the most half the length of the cannula, further preferentially at the most one-third the length of the cannula and/or no more than 5 cm around said proximal end of the cannula, further preferentially at most 3 cm and still further preferentially no more than 1 cm. This thereby advantageously enables preventing contact with the cannula, in particular the hollow needle of the cannula, and thus the hygienics and/or treatment quality increased. One advantage of the thus achieved spacing of the gripper elements from the cannula's distal end can in particular be in the hygienic requirements on the gripper elements being able to be reduced, whereby in particular the operation and/or the construction of the gripper apparatus can be simplified while maintaining the same or increased hygienics in terms of the cannula and the treating of the patient.

According to one preferential further development, the moving device comprises or consists of an electric actuator—in particular an electric motor, preferably a stepper motor—with which the movement of the gripper elements can advantageously be electrically controlled.

Preferably, the moving device comprises a spring element which advantageously enables the gripper element to be brought into engagement with the cannula holder, maintain the engagement and/or disengage the engagement. This thereby in particular enables simplifying the construction of a controllable, in particular electronically, actuator. The gripper apparatus is also preferably designed to maintain engagement with the spring element, in particular without the additional activating of the controllable actuator, this thereby enabling the achieving of passively retaining the grasped cannula.

According to one preferential further development, the—in particular exactly two—gripper elements are arranged adjacent one another and each have a respective receiving side faced away from the respective other far side, which is preferably an underside and corresponds to an underside of the cannula, as well as a cavity for at least partially receiving the cannula holder. In addition, a grip region is formed on each opposite far side. The cavity thereby extends from the one opposite side to the other opposite side and through the grip regions and is open to the receiving side of the two gripper elements so that a middle section of the cannula holder can be introduced into the cavity from the receiving side of the two gripper elements in a receiving state of the gripper apparatus. Furthermore, for the gripping of the cannula after the middle section of the cannula holder has been introduced into the cavity, the moving device is designed to move the two gripper elements away from each other along the middle section and in each case in the direction of the opposite sides until at least the respective grip region form-fits and/or force-fits with the corresponding region of the cannula holder. One advantage of gripping by means of moving the gripper elements away from one another can in particular be in that the gripper apparatus; i.e. in particular the gripper elements, have less of a spatial extension in the receiving state as in the gripping state, whereby reliability during receiving and/or gripping can be increased, for instance because no obstructions aside from the cannula holder can end up in the receiving area. An endpoint at which at least a respective grip region form-fits and/or force-fits with the corresponding region of the cannula holder can also be defined during gripping, preferably by means of an end position sensing device, which can in particular comprise measuring based on radiation, in particular light, or energy, and the gripping thereby advantageously adapted dynamically to different cannula holder sizes, in particular lengths, in particular the middle section thereof. Moreover, one advantage of the downward directed cavity can in particular be that the lower area below the underside of the cannula can remain at least substantially free. The cannula can thereby also be advantageously grabbed from a storage space by the gripper apparatus being driven over the storage space and lowered to same such that the cannula holder is introduced into the cavity.

Preferably the grip regions are in each case oriented either to the proximal or to the distal end of the cannula, wherein in particular the force for the form-fitting and/or force-fitting retention of the cannula acts at least substantially along a longitudinal axis of the cannula, whereby in particular an unwanted change in the orientation of the longitudinal axis due to laterally acting forces, thus in particular a change in the angle of the cannula to the patient—particularly during cannulation—can be prevented and the safety and/or quality of the treatment can thus be increased.

Preferably, the grip regions and/or the corresponding regions of the cannula holder are rotationally symmetric relative to the longitudinal axis of the cannula, whereby the cannula advantageously rotates about the longitudinal axis freely—or pursuant to the symmetry angle of the rotational symmetry—and can thus be oriented as well as can preferably be fixed in the selected rotational position in the gripping state by force and/or the cannula can be received in the receiving area independent of its rotational position about its longitudinal axis.

Preferably, the grip regions and/or the corresponding regions of the cannula holder are asymmetrical relative to the longitudinal axis of the cannula, whereby the rotational position of the cannula about its longitudinal axis is advantageously predetermined at least in the gripping state. The grip regions and/or the corresponding regions thereby preferably have a centering geometry which, should the rotational position of the cannula deviate from the predetermined rotational position during gripping due to the asymmetry, induces the grip regions and the corresponding regions to slide alongside each another and thus rotate the cannula about the longitudinal axis until the predetermined rotational position is reached.

According to one preferential further development, the gripper apparatus further comprises a receiving area for at least partially receiving the cannula holder. The—in particular exactly two—gripper elements are thereby arranged adjacent to the receiving area and each have a respective side facing the receiving area. In addition, at least one grip region is formed on the facing sides. Furthermore, for the gripping of the cannula after the cannula holder has been arranged in the receiving area, the moving device is designed to move the gripper elements toward each other as well as move the at least one grip region toward the corresponding region of the cannula holder relative to said cannula holder until at least the at least one grip region form-fits and/or force-fits to the corresponding region. One advantage of the movement toward each other can in particular be that of a compressive stress acting upon the cannula holder during gripping, thereby enabling materials to be used for the cannula holder which are stable in terms of pressure loads but not necessarily to the same extent as far as tensile loads. In particular, using materials which are stable to pressure load for the cannula holder—for instance preferably rigid, incompressible materials—enables realizing higher strength compared to shear force and/or tensile force loads and thereby in particular a force-fit fixation of the cannula holder by means of the gripper elements.

Preferably, given at least two grip regions, all but one grip region and/or the region of the cannula holder corresponding thereto have a greater play relative to said one grip region or region of the cannula holder respectively so that the position and/or orientation of the cannula holder in the gripping state is at least substantially determined by said one grip region or cannula holder region respectively while the remaining areas have freedom of movement by virtue of said play. This advantageously enables preventing an overdefining of the position and/or orientation of the cannula holder and/or the improper positioning or orientation and/or forces due to deficient fit.

According to one preferential further development, at least in the gripping state and preferably while gripping, a first of the gripper elements is arranged on a first longitudinal side of the cannula and a second of the gripper elements is arranged on a second longitudinal side of the cannula opposite from the first longitudinal side. A grip region is in each case thereby formed on the facing side of the first and/or second gripper element.

A cannula usually has two longitudinal sides, a first longitudinal side and a second longitudinal side. The longitudinal sides are defined by a plane of the cannula which runs between the distal and the proximal end of the cannula and/or encloses with the longitudinal axis an angle of no more than 45°, preferably at most 15°, preferably at most 5°, and further preferentially 0°, and situated on the one or respectively other side of the plane. This plane also runs from the upper side of the cannula to the underside of the cannula and encloses an angle between 45° and 135°, preferably between 70° and 110° and preferably between 85° and 95°, particularly with an area which separates an upper region above the upper side of the cannula from a lower region below the underside of the cannula, and is preferably at least substantially orthogonal to this area.

One advantage of the arrangement of the gripper elements on the first and the second longitudinal side can in particular be that the gripper elements can be drawn near to the cannula at the side and in particular a lower area below the underside of the cannula can thereby remain at least substantially free. The rotational position relative to the longitudinal axis of the cannula and relative to the surface which separates the upper area from a lower area can thus also be advantageously specified.

Preferably the grip regions at the first and the second longitudinal side and the corresponding regions of the cannula holder are asymmetrical with respect to a transverse axis of the cannula which runs from the grip regions at the first longitudinal side to the grip regions at the second longitudinal side. The asymmetrical grip regions and corresponding regions of the cannula holder thereby advantageously enable a specifying of the rotational position relative to the transverse axis.

Also preferably, gripper elements with grip regions at one of the longitudinal sides are moved along the transverse axis toward the opposite gripper elements at the other of the longitudinal sides. This advantageously enables a simple realization of a gripper apparatus which is rotatable about said transverse axis.

According to one preferential further development, the first and the second gripper elements are of pincer-like form. Furthermore, the first and the second gripper element are rotatably mounted about a rotational axis in the direction of a longitudinal axis of the cannula relative to one another. In particular, this bearing enables realizing a pincer-like motion. One advantage of the pincer-like design to the gripper elements can in particular be that the rotation about the rotational axis and the bearing required for same is, mechanically speaking, particularly sturdy, proven and/or reliable, whereby particularly the automated gripping can be improved—i.e. in particular made more reliable—and/or a mechanically simpler design and one thereby also of lower weight compared to designs with linear movements can be realized.

According to one preferential further development, a first of the gripper elements is arranged in an upper area above the upper side of the cannula and a second of the gripper elements is arranged in a lower area below an underside of the cannula at least in the gripping state. Furthermore, the moving device is designed to move the second gripper element along a longitudinal axis of the cannula as well as toward the upper area. One advantage of the arrangement of the second gripper element in the lower area as well as said second gripper element moving in the direction of the upper area can in particular be that when gripping the cannula, the cannula can first be brought into the receiving area by a movement from the proximal end towards the distal end and the cannula can thereafter be fixed to the first gripper element by moving the second gripper element. In particular the position and rotational position relative to a transverse axis, which extends in the separation plane between the upper and the lower area and is at least substantially orthogonal to a longitudinal axis of the cannula, can thereby be reliably specified and deviations therefrom countered by means of the force during gripping. Given appropriate grip regions—i.e. in particular grip regions having a centering geometry and/or an asymmetrical form—also the rotational position relative to the longitudinal axis and/or a vertical axis pointing from the upper area to the lower area can in particular be specified.

Preferably, a cannula holder comprises a cannula or, respectively, one or more engaging elements, in particular receiving bores, for a cannula.

In accordance with one preferential further development, one or more first of the preferably at least three gripper elements comprise grip regions formed as corresponding engaging elements to the engaging elements of the cannula holder. Furthermore, one or more second gripper elements is/are arranged in each case with respect to the first gripper elements such that when gripping; i.e. upon the engaging of the first gripper elements, they support the cannula on or by means of the cannula holder, and thereby effect an opposing force counteracting the engaging force. One advantage of the engaging can in particular lie in fixation via engaging being well-established and thus reliable. Engaging also enables achieving a passive retention of the cannula, in particular no controllable actuator thus needs to be activated or continued post-engagement in order to maintain the engagement of the gripper elements and the cannula holder and thus the fixation of the cannula.

Preferably, a cannula holder comprises a cannula or, respectively, an internal thread for a cannula.

According to one preferential further development, a first of the, in particular exactly two, gripper elements comprises a spindle having an external thread which corresponds to an internal thread of the cannula holder. Furthermore, a second of the gripper elements has an internal thread corresponding to the external thread of the spindle. The moving device is thereby designed to screw at least a part of the spindle into the internal thread during gripping. One advantage of the screw coupling thus achieved can in particular be that the threaded connection is a particularly robust and thus reliable cannula grip and/or can be combined with a centering geometry such that the cannula holder can also be screwed to the gripper apparatus by means of the spindle, even in the case of initially slight divergency.

A second aspect of the invention relates to a cannula holder, in particular for a gripper apparatus according to the first aspect of the invention. The cannula holder comprises one or more regions which correspond to grip regions of the gripper apparatus and which are preferably of a permanent form. The cannula holder additionally comprises a connecting area for connecting, in particular integrally, to a cannula.

The previously cited possible advantages as well as embodiments, further developments or variants of the first aspect of the invention also apply correspondingly to the inventive cannula holder. Inversely, the following cited possible advantages as well as embodiments, further developments or variants of a cannula holder according to an embodiment of the second aspect of the invention also apply correspondingly to a gripper apparatus according to an embodiment of the first aspect of the invention having or respectively for a cannula having such a cannula holder.

According to one preferential embodiment, the cannula holder is made of a disinfectable material. Preferably, the cannula holder is made from a plastic. Also preferably, the cannula holder is already connected to a cannula in the manufacturing process and both disinfected together and thereafter packaged. This advantageously enables improving the hygienics and/or increasing the treatment quality or treatment safety.

In one preferential embodiment, the connecting area is spaced at a distance from the cannula holder regions corresponding to the grip regions such that the gripper elements of the gripper apparatus are spaced apart at least in the gripping state and preferably when gripping the cannula, in particular the hollow needle of the cannula. One advantage of this spacing can in particular be in being able to prevent contaminants via components of the gripper apparatus during gripping or at least in the gripping state, whereby treatment safety in particular can be increased and/or the hygiene requirements on the gripper apparatus can be reduced compared to a solution in which the gripper apparatus contacts component parts of the cannula—in particular those intended to be inserted into the patient—and thus being able to simplify the design requirements and/or reduce manufacturing costs.

A third aspect of the invention relates to a cannulation robot for the automated cannulation of a patient's blood vessel having a gripper apparatus according to the first aspect of the invention.

The previously cited possible advantages as well as embodiments, further developments or variants of the first and/or second aspect of the invention also apply correspondingly to the inventive cannulation robot.

A cannulation robot is an apparatus which automatically; i.e. at least intermittently or continuously, performs at least one cannulation process step in a patient blood vessel, or several or all intended process steps, without the intervention of a human operator, e.g. medical personnel. This thereby ensues in particular by the program parameters of the automated cannulation being accordingly selected by the system and/or by the user. One process step in the cannulation is in particular technically implemented by an apparatus component of the cannulation robot, e.g. a tool device, specifically configured for said process step and is selected from the group comprising the possible process steps P1, P2, P3 . . . , without this numbering defining a sequential ordering:

P1: Using an accessory kit to perform the cannulation which is selected prior to commencing the automated cannulation based on the registered patient identifier; this selection can have been made previously by means of an optional pick-and-place system of the system for selecting an accessory kit and/or equipping an accessory holder, in particular an accessory box; the accessory kit can have been provided beforehand as a function of the registered patient identifier by an optional sorting apparatus of the system selecting the accessories contained in the accessory kit from an optional storage apparatus of the system for storing accessories; the accessory kit can contain one or more medical accessories, in particular gauze, swabs, adhesive tape; the accessories of this accessory kit can be gathered as a function of the registered patient identifier and/or as a function of patient-specific treatment data derived from the registered patient identifier; the use of this accessory kit by the cannulation robot is a process step of the automated cannulation and can provide for the accessories of the accessory kit to be automatically extracted from predetermined positions of an accessory holder/box, in particular by the appropriate program parameters being selected as a function of the registered patient identifier and suitable for extraction; an optional pick-and-place device of the cannulation robot being in particular used to that end which is configured to extract the accessories out of the accessory holder and/or configured to equip one or more optional tool devices of the cannulation robot;

P2: Spatially fixating a part of the patient's body containing the blood vessel, in particular an arteriovenous fistula; the program parameters of the automated cannulation can be selected here as a function of the registered patient identifier, thus individual to each patient, these program parameters setting beforehand the position or the spacing of one or more optional fixation devices of the cannulation robot based on a previously determined location or on predetermined spacings on the patient's body part so as to achieve suitable fixation; the fixation taking place in the treatment chamber of the cannulation robot in which the patient's body part rests for the at least one ensuing cannulation;

P3: Using stored—in particular in a patient database—patient data in order to determine information on past cannulation process steps in the patient's vasculature (historical data), and preferably define the cannulation to occur, in particular the program parameters thereby used, based on this historical data; such historical data containing in particular the location of one or more of the patient's blood vessels previously measured by an optional measuring device of the cannulation robot for measuring the location and/or dimensions of at least one blood vessel under the patient's skin (vascular structure measuring device), and providing same in particular as patient data; such historical data containing in particular information on the location and condition of further puncture sites on the patient's body which is in particular provided as patient data; the vascular structure measuring device being able to be designed to detect the location and/or dimensions of at least one blood vessel under the patient's skin by means of ultrasound or by means of optical radiation;

P4: Identifying the blood vessel under the patient's skin suitable for the blood withdrawal, in particular selecting a suitable insertion site on the skin for the cannulation of said blood vessel; the program parameters of the automated cannulation can hereby be selected as a function of the registered patient identifier, thus individual to the specific patient, by the cannulation planned for the registered patient being selected on the basis of at least one patient-specific treatment parameter; for example with a patient planned for hemodialysis; a treatment parameter can encode the patient's necessity for hemodialysis; the cannulation of an arteriovenous blood vessel can be planned by evaluating the treatment parameter; same being identified; the identification can for example ensue in the control system by a program-controlled analysis of an image obtained by a vascular structure measuring device;

P5: Disinfecting the skin of the patient's body part containing the blood vessel; the program parameters of the automated cannulation can hereby be selected as a function of the registered patient identifier, thus individual to the patient, by a disinfecting process being specifically selected for the patient's type of skin or skin morphology which is for example characterized by the length of the treatment or the amount and nature of the disinfecting process employed; treatment data specific to the patient can also be considered; a disinfecting device which is optional with the cannulation robot or separate therefrom and equipped to perform the cited function can be used for the cited disinfection; the type of skin or skin morphology of the patient being preferably known in particular as patient data in the patient database;

P6: Physically treating the patient's body part containing the blood vessel in preparation for the cannulation, in particular stemming the blood flow of the body part, applying pressure to the body part, controlling the temperature of the body part, positioning the immobilized body part; the program parameters of the automated cannulation can hereby be selected as a function of the registered patient identifier, thus individual to the specific patient, by drawing on preparation data specific to the planned patient treatment, e.g. hemodialysis, or which can be taken from the patient database as known preparation data; this preparing for the cannulation of the body part being in particular performed by an optionally provided prepping device of the cannulation robot correspondingly configured for this purpose;

P7: Particularly preferential: Puncturing the blood vessel, in particular an arteriovenous fistula; preferably a first venipuncture and cannulation occurring automatically for withdrawing blood from the blood vessel and a second venipuncture and cannulation occurring automatically for the return of the blood, in particular in the case of hemodialysis; the program parameters of the automated cannulation can hereby be selected as a function of the registered patient identifier, thus individual to the specific patient, by the program parameters defining a patient-dependent motion control for a robotic tool arm optionally provided in the cannulation robot, by means of which a medical accessory such as for instance an injection needle can for example be grasped by the tool arm and positioned on the body part, with the injection needle having been previously selected and prepared specific to the patient; two cannulation robots can be set up for puncturing blood vessels at different parts of the body by, for example, a first cannulation robot being configured for cannulation on an arm and a second cannulation robot being configured for cannulation on a leg; the selection of the appropriate cannulation robot can ensue in patient-specific and/or treatment-specific manner;

P8: Withdrawing blood from the cannulated blood vessel and transporting the blood in at least one blood transport device or in at least one sample container; the program parameters of the automated cannulation can hereby be selected as a function of the registered patient identifier, thus individual to the specific patient, by a suitable blood transport device or suitable sample container being preselected as a function of patient-specific treatment data and then utilized in suitable manner by the cannulation robot; the cannulation robot and the control system can be configured thereto by an appropriate selection of the program parameters to provide at least one sample container based on treatment data for the subsequent, preferably automatic and system-controlled, treatment, in particular diagnostics;

P9: Grasping a cannula by means of a gripper apparatus of the cannulation robot.

The term "cannulation" refers to a procedure in which a cannula is inserted into the blood vessel in the patient's body part by puncturing the skin and venipuncturing the blood vessel wall so that the distal end of the cannula is disposed in the blood vessel and the proximal end of the cannula is disposed on the outside of the body part so that a fluid connection can be established between the cannula and the blood vessel, by means of which fluid, in particular blood and/or fluid media, can be exchanged via the fluid connection. The "exchange" of fluid in this context means that fluid from the patient's blood circulation is conveyed to an extracorporeal fluid system, i.e. situated external of the patient's body, in particular for fluid storage or fluid conduction, and/or includes conveying fluid from the extracorporeal system into the blood circulation.

Chronically ill patients need regularly repeated vasculature cannulation in order to ensure the necessary treatment. One such chronic illness is kidney failure which leads, among other things, to the loss of the blood's natural purifying function. Technical solutions can be substituted in its place. Hemodialysis devices are extracorporeal filtering units serving as artificial kidneys into which the blood of the patent is conducted in order to be cleansed and treated before being returned to the patient's blood circulation. Blood is normally withdrawn and returned via an artificial subcutaneous connection surgically created between a vein and an artery in an arm or a leg of the patient. This connection can be composed of a section of the patient's own vasculature prepared for same or can consist of an artificial material and is referred to as a fistula or arteriovenous fistula respectively (AV fistula, AVF).

The most commonly used permanent vascular access in chronic hemodialysis patients is a native arteriovenous fistula. After the native arteriovenous fistula is placed, it become stronger due to the increased blood flow, whereby repeated cannulation for the dialysis treatment becomes easier.

Hemodialysis must be performed regularly, typically a few days apart. This leads to high mechanical stress on the blood vessel or arteriovenous fistula respectively. Different techniques are known to create access to a blood vessel or arteriovenous fistula respectively, these aiming to be as gentle as possible on the vessel over the course of the repeated cannulation. In rope ladder cannulation, a new cannulation site located at a distance from the previous site, e.g. about 2 cm, is sought for each treatment. In this method, the series of punctures are usually started at the lower end of the vessel and then continue upward until reaching the upper end and the process then started again from below. The practitioner must thereby precisely follow the positioning pattern so as to allow the venipunctured vessel sites to heal. In contrast, in the buttonhole technique, a needle is always inserted into the exact same spot at the exact same angle. Over time, a scar tunnel thus develops which continually displaces the thrombus forming in cannulation and thus becomes more resilient. It has been found that buttonhole technique results can be improved if the cannulation is always performed by the same treatment personnel.

Due to the frequency of cannulation with hemodialysis patients, the arteriovenous fistula is subject in general to high stress, independent of the venipuncture technique, same which can lead to changes in the surface of the skin and the condition of the arteriovenous fistula and how they progress.

One advantage of the cannulation robot can in particular be seen in that, particularly when treating chronic illnesses—in particular with hemodialysis patients—, automated cannulation can reduce the workload of the medical personnel and/or provide a consistently high cannulation precision, whereby in particular treatment quality and/or treatment safety can be increased.

A fourth aspect of the invention relates to a method for the automated gripping of a cannula having the following method steps. In one method step, a cannula with a cannula holder is provided or a cannula without a cannula holder is first connected to a cannula holder and then provided. In one method step, the cannula with cannula holder is arranged in a receiving area of a gripper apparatus. In one method step, at least two gripper elements of the gripper apparatus are moved relative to each other and at least one of the gripper elements relative to the cannula holder until at least one of the gripper elements engages with the cannula holder.

The previously cited possible advantages as well as embodiments, further developments or variants of the previous aspects of the invention also apply correspondingly to the inventive method for automatically gripping a cannula. Inversely, possible advantages as well as embodiments, further developments or variants of the method according to one embodiment of the fourth aspect of the invention also apply correspondingly to the previous aspects of the invention.

Preferably, in one method step, a cannulation robot is equipped with or comprises a gripper apparatus, particularly in accordance with the first aspect of the invention.

Preferably, the cannulation robot can also comprise a robotic tool arm, by means of which the latter moves the gripping apparatus toward the cannula such that the cannula is disposed in the receiving area of the gripper apparatus. The cannula can thereby preferably be initially disposed on a storage space or in a storage area or accessory set.

Preferably and alternatively to disposing the cannula with cannula holder in the receiving area, a cannula holder can also be initially disposed in a receiving area, in particular on the gripper elements, and be subsequently disposed in the receiving area and ultimately grasped by means of the gripper elements interacting with the cannula holder of the cannula, which initially exhibits no cannula holder.

In particular, the providing of the respective means—in particular the cannulation robot, a robotic tool arm, the gripper apparatus and/or the cannula holder—can be a part of the method, thus in particular a method step, or these means provided prior to implementing the method.

According to one preferential further development, the gripper apparatus is driven by means of a robotic tool arm of a cannulation robot to the proximal end of the cannula and at least one second of the gripper elements, and preferably the gripper apparatus, then moved along a longitudinal axis of the cannula toward the distal end of the cannula until the cannula holder is arranged in the receiving area. An area surrounding the distal end of the cannula thus advantageously remains free upon arranging the cannula in the receiving area, whereby in particular contamination can be avoided and thus hygienics increased. Furthermore, particularly the cannula, in particular a hollow needle of the cannula, can thereby be provided with a protective cover which protects same against contamination.

Preferably, the protective cover is not removed until directly before cannulation; i.e. in the present case, directly before blood vessel puncturing, or at least not removed until after grasping or in the gripping state. In addition, the cannulation robot or the gripper apparatus can comprise a means for removing the protective cover, in particular a removal means—for instance additional gripper elements for grabbing and pulling off the protective cover.

According to one preferential further development, a tube, in particular an infusion tube, is automatically fluidly connected to a connector part of the cannula prior to, during or after the cannulation as well as prior to the engagement between the cannula holder and gripper apparatus being disengaged. One advantage of connecting while the cannula holder is engaged with the gripper apparatus can in particular lie in being able to reduce the mechanical stressing of the cannulated blood vessel. One advantage of connecting prior to the cannulation or at least before an access to the blood vessel is created can in particular lie in not needing to prevent blood leakage and the connecting thereby being made easier and/or the cannula not needing to comprise any additional device such as a valve or control lever to prevent blood leakage.

Preferably, the cannula holder comprises a connector part designed for fluid connection with a tube. In particular, said connector part can be the connector part of the cannula for the tube.

The invention also expressly relates to a system for the treatment and in particular the cannulation of a patient. Said system comprises a cannulation robot for the automated cannulation of a patient's blood vessel, in particular according to the third aspect of the invention, one or more cannulas, as well as one or more cannula holders, in particular according to the second aspect of the invention, and at least one gripper apparatus for a cannula having a cannula holder, in particular according to the first aspect of the invention. Preferably the cannulas are in each case integrally connected to one of the cannula holders.

The system also preferably comprises at least one storage area for cannulas, in particular cannulas with cannula holders. Preferably, the system is designed to realize a method in accordance with the fourth aspect of the invention. In particular, the cannulation robot can comprise a robotic tool arm to that end, same being equipped with the gripper apparatus and which extracts a cannula with cannula holder from the storage area by means of said tool arm, thus in particular grasps by means of the gripper apparatus.

As defined by the invention, "configured" refers to an apparatus not only being in principle suited to fulfill a specific function—for instance only after a specific program code has been loaded; i.e. the apparatus programmed, or the apparatus formed in a specific way—but the apparatus already possesses all the means necessary in order to actually fulfill the function. Preferably, the apparatus is to that end already programmed with a program code for said function and/or already configured and/or arranged and/or exhibits such a configuration thereto that the apparatus actually fulfills the function.

"Treatment of a patient" in the sense of the invention refers to at least one medical; i.e. in particular therapeutic, diagnostic or cosmetic, procedure which effects changes to the body and/or health of the patient or by means of which the state of the patient's health is determined. A treatment is in particular an administration of medicinal products, a cannulation, a blood purification procedure such as dialysis, an operation and/or an examination of the patient.

A "group of treatments" in the sense of the invention can be respective specific operations, therapy for a specific illness, the initial examination of a patient, or a dialysis treatment which in turn can comprise sub-groups, in particular hemodialysis, hemofiltration, hemodiafiltration, hemoperfusion or peritoneal dialysis treatments.

As defined by the invention, an "individual involved in the treatment" can in particular be understood as an attending person, for instance a physician, or an individual providing treatment support, for instance a nurse. In particular, the patient to be treated can himself also be an individual involved in the treatment or an attending person.

To be understood by a "data processing apparatus" in the sense of the invention is at least one apparatus configured to process data; i.e. in particular to receive data, store received data, read out stored data, transform received and/or stored and/or read data by means of logical and/or mathematical operations, store transformed data, and/or output transformed and/or read data. Preferably, such a data processing device is programmable; i.e. a program code in particular at least partially specifies the method for processing the data and at least part of said program code is modifiable.

Preferably, the data processing apparatus is a commercially available computer. Further preferentially, the data processing apparatus comprises at least one data processor—i.e. a central processing unit—, in particular a microprocessor, a non-volatile—i.e. in particular permanent—data storage, in particular a hard disk, a read-only memory (ROM) or a drive with a data medium, as well as at least one hardware interface. The data processing apparatus also preferably comprises a volatile electrical data storage, in particular as main memory, preferably a semiconductor memory, in particular with integrated capacitors and/or flip-flops (bistable multivibrators) for data storage, for instance dynamic RAM or static RAM.

In the sense of the invention, a "data storage apparatus" is an apparatus for storing data. Same is in particular designed to form a data link with a further apparatus, particularly a data processing apparatus, and/or comprises a data link to the further apparatus, wherein data can be transmitted to the data storage apparatus from the further apparatus for storage by means of the data link and/or data can be transmitted from the data storage apparatus to the further apparatus for retrieval. Preferably, the data storage apparatus comprises at least one non-volatile data storage. Also preferably, the data storage apparatus comprises at least one volatile electrical data storage.

A communication device is preferably configured to transmit and/or receive data, in particular for data exchange over a data link provided by the communication device, particularly for a remote data link to a remote device. The data link, in particular remote data link, can be established by a restricted (in particular intranet) or global network of computers (in particular a WAN and/or the internet). The data link, in particular remote data link, can also be established by wireless connection, in particular radio link. The data link, in particular remote data link, can in particular be established by mobile radio connection.

A data link connects in particular two data processing units, in particular two data processing devices or apparatus, in a way so as to enable the exchange of data between the units, either unidirectionally or bidirectionally. The data link can be realized in wired or wireless manner, in particular as a radio link. A remote data connection connects in particular two data processing units, particularly two data processing devices, disposed at a distance from one another, thus not being component parts of the same device, in particular the same user interface device or the same control system, if the cited devices are realized as separate units. A data link, in particular remote data link, of one device to another device is preferably realized by a direct connection between the two devices or by an indirect connection of the two devices such that a third device is connected between the two devices in order to pass on the data. A remote data link can in particular be realized by a network of computers with which the devices connected by the remote data link are interconnected via the network. The network can be a restricted network, e.g. an intranet, or global network, in particular a WAN and/or the internet.

In the sense of the invention, an "interface device" serves the connection of two units—in particular including systems, apparatus, devices or mechanisms, particularly having such units—, respectively capable of processing signals, in particular information, particularly data, thus in particular sending and/or receiving. An interface device can comprise at least one hardware interface and in particular be integrated into a physical device unit as a component part.

Further advantages, features and possible applications of the present invention are yielded by the following detailed description of at least one example embodiment and/or by the figures. Unless otherwise described or contextually indicated otherwise, the same reference numerals are substantially used to identify equivalent components in the embodiments.

Thereby shown, to some extent schematized:

FIG. 1A a side view of a cannula having an example embodiment of the cannula holder according to the invention;

FIG. 1B a frontal view of a gripper element of an example embodiment of the gripper apparatus according to the invention;

FIG. 1C a sectional view through two gripper elements of an example embodiment of the inventive gripper apparatus in the receiving state together with a cannula with cannula holder;

FIG. 1D a sectional view through two gripper elements of an example embodiment of the inventive gripper apparatus in the gripping state together with a cannula with cannula holder;

FIG. 2A a view from above of an example embodiment of the inventive gripper apparatus together with a cannula having an example embodiment of the inventive cannula holder;

FIG. 2B a side view of the gripper apparatus as well as a side view of the cannula holder;

FIG. 2C a view from above of the gripper apparatus in the gripping state gripping the cannula holder;

FIG. 2D a pivoting of the gripper apparatus with grasped cannula in side view;

FIG. 3A a view from above of a cannula having a further example embodiment of the cannula holder according to the invention;

FIG. 3B a sectional view through a further example embodiment of the inventive gripper apparatus in the receiving state together with a cannula with cannula holder in side view;

FIG. 4A a side view of a cannula having a further example embodiment of the inventive cannula holder;

FIG. 4B a frontal view of a further example embodiment of the inventive gripper apparatus;

FIG. 4C a detail of the gripper apparatus in the gripping state gripping the cannula holder depicted in a frontal view;

FIG. 5A a side view of a cannula with a further example embodiment of the inventive cannula holder;

FIG. 5B a view of said inventive cannula holder from above;

FIG. 5C a sectional view through a further example embodiment of the inventive gripper apparatus in the receiving state together with a sectional view through the cannula holder depicted in a frontal view;

FIG. 5D the sectional view through the gripper apparatus, whereby same is in the gripping state and gripping the cannula holder;

FIG. 6A a frontal view of the gripper apparatus releasing the engagement with the cannula holder;

FIG. 6B an alternative variant of a gripper element of said gripper apparatus in a sectional view and two side depictions;

FIG. 7A a side view of a cannula having a further example embodiment of the inventive cannula holder;

FIG. 7B a view of said inventive cannula holder from above;

FIG. 7C a sectional view through a further example embodiment of the inventive gripper apparatus in the receiving state together with a sectional view through the cannula holder depicted in a frontal view;

FIG. 7D the sectional view through said gripper apparatus, whereby same is in the gripping state and gripping the cannula holder;

FIG. 8 an example embodiment of an inventive cannulation robot;

FIG. 9 an example embodiment of the method according to the invention for the automated gripping of a cannula;

FIG. 10A an example embodiment of the inventive cannulation robot as well as an example embodiment of the inventive cannula holder, which is connected to a cannula, in a method step of an example embodiment of the inventive method for the automated gripping of a cannula;

FIG. 10B said cannulation robot and cannula holder in a further method step of the method;

FIG. 10C the gripper apparatus of the cannulation robot together with the cannula holder in yet another further method step of the method.

FIG. 1A depicts a side view of a cannula 220 with an example embodiment of the cannula holder 200 according to the invention. A longitudinal axis 212 of the cannula 220 extends from the proximal end 224 to the distal end 222 of the cannula 220. The cannula has a beveled tip at its distal end 222 for inserting into tissue. In particular, an upper side 226 and an underside 228 can be defined for the cannula 220 relative to the position to a patient or relative to the beveled tip as described above. The underside 228 is thereby that side at which the tip ends. Preferably, a cannula is positioned relative to the patient for cannulation such that the end of the beveled tip is closer to the patient than the neck of the beveled tip which is situated farther toward the proximal end 224 of the cannula. In this case, the definitions for the upper side and the underside of the cannula correspond.

The cannula holder 200 comprises two regions 230, 232, which correspond to corresponding regions of a gripper apparatus, a connecting area 240, which is integrally connected to the cannula 220, and a middle section 242. The two regions 230, 232 face each other, are spaced apart via middle section 242, and taper toward the middle section 242.

Preferably, the cannula holder 200 is rotationally symmetrical, in particular cylindrically, around longitudinal axis 212. Preferably, the regions 230, 232 are of trapezoidal or conical shape, in the shape of a distorted cone having an oval surface area, or in the shape of a pyramid, in particular having a surface area of an irregular triangle. The rotational symmetry thus enables a gripper apparatus to grab the cannula holder 200, and thus the cannula 220, at different rotational positions in which the cannula holder 200 is rotationally symmetric while an asymmetry enables predefining a specific rotational position.

Preferably, the cannula holder 200 is made of a disinfectable plastic, in particular PEEK or polypropylene.

Preferably, the cannula holder 200 is arranged at the proximal end 224 of the cannula, which enables an area surrounding the distal end 222 of the cannula 200 to remain free during gripping or at least in the gripping state. In particular, the cannula holder 200 can initially be produced separately from the cannula 220 and then subsequently integrally connected to the cannula, for instance by melting the plastic or by means of an adhesive. Preferentially and alternatively, the cannula holder can be produced together with the cannula, whereby in particular the cannula holder is injection-molded around an area of the cannula, in particular around a region at its proximal end, in an injection-molding process. The thus connected cannula holder and cannula are preferably thereafter disinfected and sterile-packed.

FIG. 1B shows a frontal view of a gripper element 110 of an example embodiment of the gripper apparatus according to the invention, in particular for the cannula holder 200 from FIG. 1A. In the frontal view, the viewer is facing a side 114 of the gripper element 110 opposite from a side of a further gripper element of this example embodiment of the gripper apparatus. A grip region 130 of the gripper element 100 is formed on this opposite far side 114. The gripper element 110 furthermore has a receiving side, in particular underside 128, a cavity 120 for at least partially receiving the cannula holder 200, and preferably an upper side 126. When the cannula holder 200 is received in the cavity, the upper side and underside of the gripper element 110 correspond to the upper side/underside of the cannula 220. The cavity 120 extends from the far side 114 through the grip region 130 and is open to the receiving side 128 so that the middle section 242 of the cannula holder 200 can be introduced into the cavity 120 from the receiving side 128 in a receiving state of the gripping device. The longitudinal axis of the cannula 220 therefore points toward or away from the viewer and is thus not depicted in FIG. 1B. Preferably, the grip region 130 is of a permanent counterpart form to the corresponding region of the cannula holder. Thus, for a corresponding conical region, the grip region 130 is preferably formed as a cone widening toward the opposite far side 114.

FIGS. 1C and 1D depict an example embodiment of the inventive gripper apparatus 100 in a receiving state and gripping state respectively. The gripper apparatus 100 comprises two gripper elements 110, 112 which are movable relative to one another and interact to grip the cannula holder 200. The gripper elements 110, 112 correspond to the gripper element 110 from FIG. 1B. Gripper element 110 comprises, as is correspondingly described with FIG. 1B, an upper side, an underside, a cavity and a grip region 130. Accordingly, gripper element 112 comprises an upper side, an underside, a cavity and a grip region 132. The gripper elements 110, 112 are furthermore adjacently arranged and gripper element 110 exhibits a far side 114 from gripper element 112 as gripper element 112 correspondingly exhibits a far side 116 from gripper element 110.

The gripper elements are depicted in a sectional view sectioned through a plane between the respective upper side and underside and extending through the cavity as well as grip regions 130, 132. The upper sides and undersides are accordingly not depicted and, for the sake of clarity, the cavity is also without reference numeral. The cannula holder 200 is connected to a cannula 220 and is preferably the cannula holder 200 from FIG. 1A, which is rotated 90° about its longitudinal axis with respect to the upper side and the underside or, respectively, the upper side and the underside do not correspond to the upper side/underside of the gripper elements; i.e. in particular the upper side and the underside of the gripper elements are aligned with the longitudinal sides of the cannula.

In the receiving state, as depicted in FIG. 1C, the gripper elements 110, 112 are arranged at a predetermined distance from each other, or contact each other and the cavity provided to receive a part of the cannula holder 200, such that grip region 130 is arranged adjacent to corresponding region 230 of the cannula holder 200 and grip region 132 arranged adjacent to corresponding region 232.

To bring into the gripping state, the gripper elements 110, 112 are moved away from each other toward their respective opposite far sides 114, 116 and preferably along the longitudinal axis 212. Preferably, to disengage the gripping state and to bring into the receiving state, the gripper elements 110, 112 are moved toward each other, in particular until they make contact, as depicted in FIG. 1C. To that end, the gripper apparatus 100 comprises a moving device 160 which is preferably disposed, as depicted in FIG. 1D, to the side of the gripper elements or, further preferentially, at the upper side of the gripper elements, so that the receiving side; i.e. in particular the underside, remains free.

In the gripping state, as depicted in FIG. 1D, the gripper elements 110, 112 are driven so far apart from one another by means of the moving device 160 that the grip regions 130, 132 engage with the corresponding regions 230, 232 of the cannula holder 200 in form-fit and/or force-fit connection. One advantage of the arrangement of the cannula holder 200 at the proximal end 224 of the cannula as well as the driving apart of the gripper elements in an area surrounding the proximal end 224 can in particular be that an area surrounding the distal end 222 of the cannula remains free and thus in particular the risk of contamination and/or efforts to prevent contamination there can be reduced.

FIGS. 2A to 2D depict an example embodiment of the inventive gripper apparatus as well as an example embodiment of the inventive cannula holder corresponding to the gripper apparatus. Insofar as technically feasible and not specified otherwise, the arrangements, forms, variants and advantages of this example embodiment correspond in particular to those from FIGS. 1A to 1D.

As particularly visible in the FIG. 2A view from above, the gripper apparatus 100 comprises a receiving area 108 for at least partially receiving the cannula holder 200. The gripper apparatus 100 additionally comprises exactly two gripper elements 110, 112 arranged adjacent to the receiving area 108. The gripper elements 110, 112 each have a side 118 facing the receiving area 108. The respective grip region 130/132 is in each case formed on the facing side 118. Said grip regions are thereby of preferably permanent form; i.e. in particular from a durable material, as counterparts to the respective corresponding regions 230, 232 of the cannula holder 200.

The cannula holder 200 is preferably integrally, mechanically as well as fluidly connected to a cannula. In FIG. 2A, the cannula 220 is arranged with its distal end 222 at the top relative to the drawing as well as its longitudinal sides 229 to the left/right sides of the drawing plane. The cannula holder 200 is connected to the cannula 220 at the proximal end of the cannula as well as fluidly connected to a tube 250, in particular an infusion tube, whereby the cannula holder 200 creates a fluid connection between the tube 250 and the cannula 220. To connect the cannula holder 200 to the tube 250, the cannula holder 200 can preferably comprise a connector part. This connector part can in particular comprise or consist of an element for a luer lock connection so that the tube 250 and the cannula holder 200 can be screwed together.

FIG. 2A shows the gripper apparatus 100 in a receiving state. The longitudinal axis 212 of the cannula extends from the proximal end of the cannula to the distal end 222 of the cannula. The transverse axis 214 runs from one of the longitudinal sides 229 to the other of the longitudinal sides 229. In the receiving state for receiving the cannula holder 200, the gripper elements 110, 112 are spaced so far apart along the transverse axis 214 as well as from the cannula holder 200 that the cannula holder 200 can initially be introduced into the receiving area 108. When the cannula 220 with the cannula holder 200 is thereupon disposed in the receiving area 108, in particular for the gripping of the cannula, the gripper elements 110, 112 are arranged at the one or the respective other longitudinal side 229 such that the grip regions 130, 132 are adjacent to corresponding regions 230, 232.

FIG. 2B shows a side view of the example embodiments from FIG. 2A in which the transverse axis points out of the drawing plane. The gripper element 110 is thereby depicted offset from the cannula holder 200 so that it and region 230 are visible. Region 230, which corresponds to grip region 130, preferably has a D-shaped surface area and is of convex shape, thus in particular extending toward the viewer. Inversely, the grip region 130 suggested by the dotted line is likewise of D-shaped surface area albeit of concave shape in order to receive region 230. In particular, the grip region 130 and/or region 230 can have a centering geometry; i.e. in particular taper upwardly; i.e. out of the drawing plane in this representation, so that region 230 and thus the cannula holder 200 are centered relative to grip region 130 during gripping. The same also applies accordingly to (not shown here) gripper element 112, its grip region 132 as well as the corresponding region 232 of the cannula holder 200.

FIG. 2C shows the gripper apparatus 100 from FIG. 1A in a gripping state in which it grips the cannula holder 200. The gripper apparatus 100 can thereby be brought from the receiving state into the gripping state by means of a moving device 160 of the gripper apparatus 100. To that end, the moving device 160 is designed to move the gripper elements 110, 112 toward one another as well as move at least one of the grip regions relative to the cannula holder 200 in order to grip the cannula after the cannula holder 200 is disposed in the receiving area. Preferably, at least one of the gripper elements is thereby moved along the transverse axis 214. To that end, the moving device 160 preferably comprises an electrically controllable linear actuator.

Preferably, the gripper apparatus 100 moreover comprises a connecting device 170 for connecting the gripper apparatus 100 to a robotic tool arm, in particular a cannulation robot. Furthermore, the moving device 160 is preferably designed to only move gripper element 110 relative to the connecting device 170 whereas gripper element 112 is not moved relative to connecting device 170. This advantageously enables the relative position and/or orientation of the grasped cannula—relative to connecting device 170—to be specified by the gripper element 112 on the one hand while the cannula holder 200 is gripped by the movement of the gripper elements 110 and the grip regions 130, 132 are brought into engagement with the corresponding regions of the cannula holder 200.

It is in general preferential with the present invention for at least one variant of the gripper apparatus 100 embodiments to comprise a connecting device 170. Further preferential is for at least one gripper element, in particular exactly one gripper element, of the at least two gripper elements 110, 112 to be rigid relative to the connecting device 170; i.e. in particular immovable by the moving device 160, whereby the relative position and/or orientation of the cannula with cannula holder is/are advantageously predefined by this rigid gripper element. This advantageously enables in particular simplifying the motion control of a robotic tool arm, to which the gripper apparatus 100 is connected by means of the connecting device 170, because with the known position and/or orientation of the tool arm, and thereby connecting device 170 and thus the at least one gripper element, also the position and/or orientation of the cannula holder as well as cannula is known.

Figure 1:
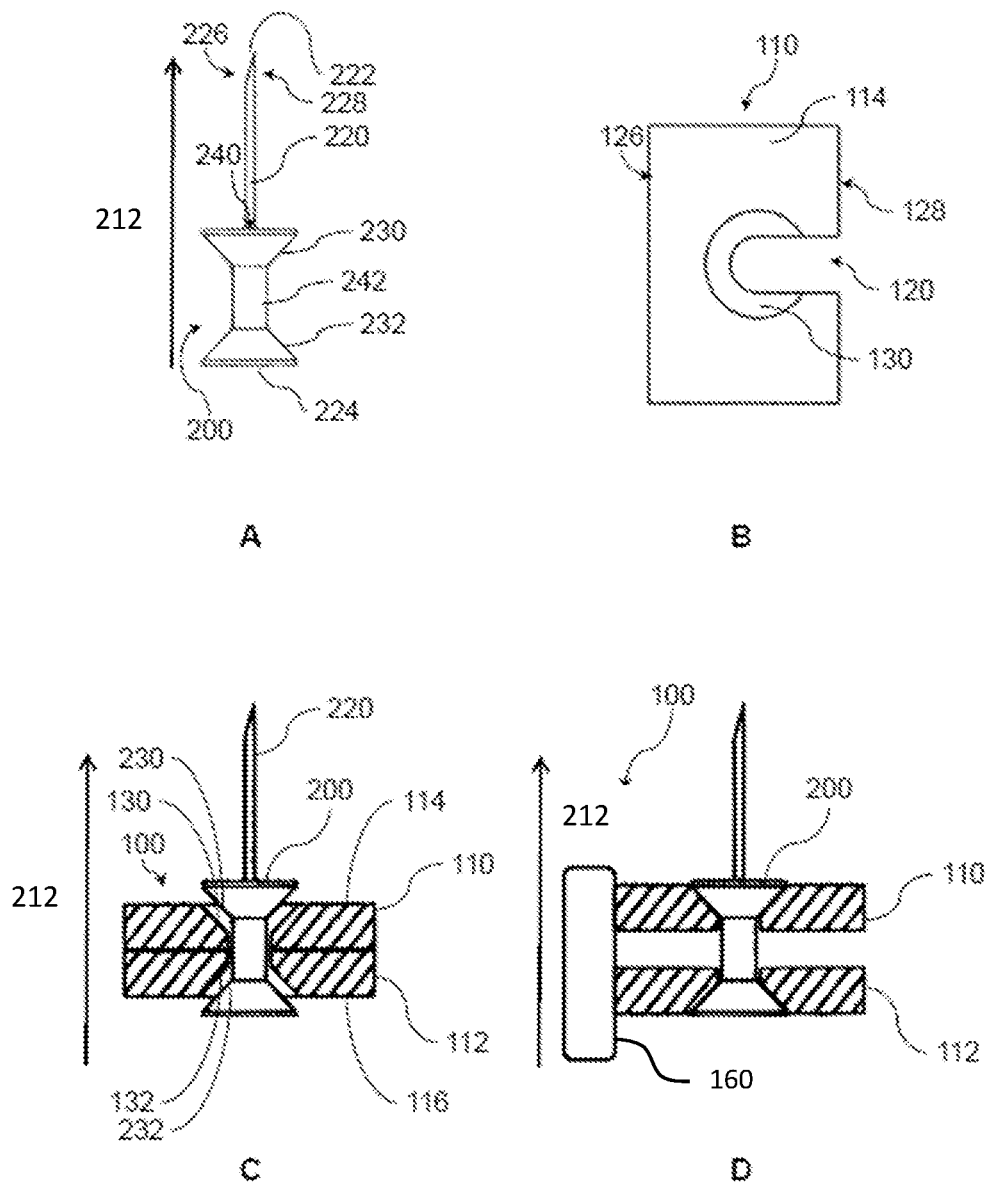
Figure 2:
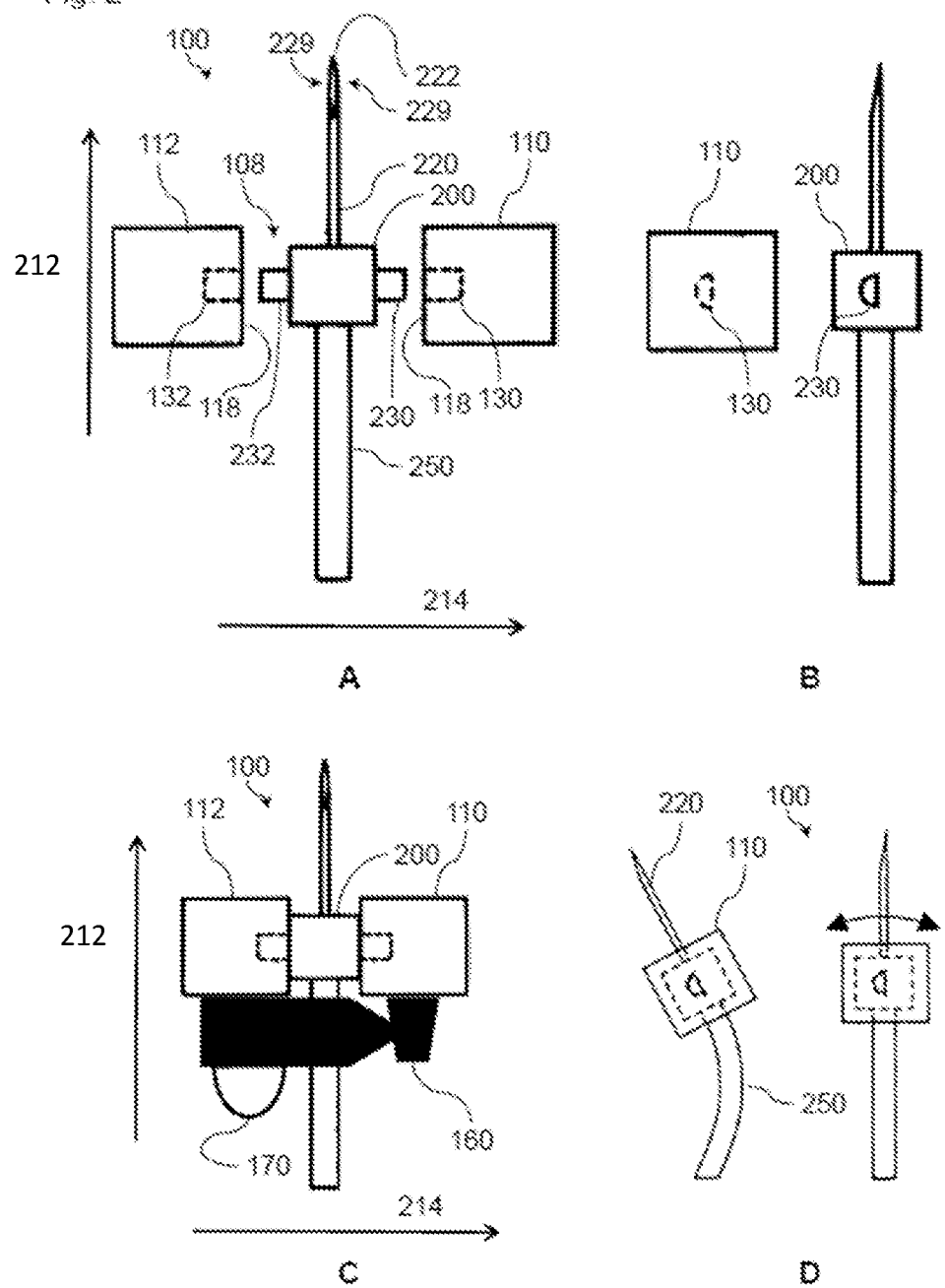
FIG. 2D illustrates a pivoting of the gripper apparatus 100 as well as the cannula 220 about the transverse axis in a side view in which the transverse axis points toward the viewer and is thus not depicted.
Figure 3:
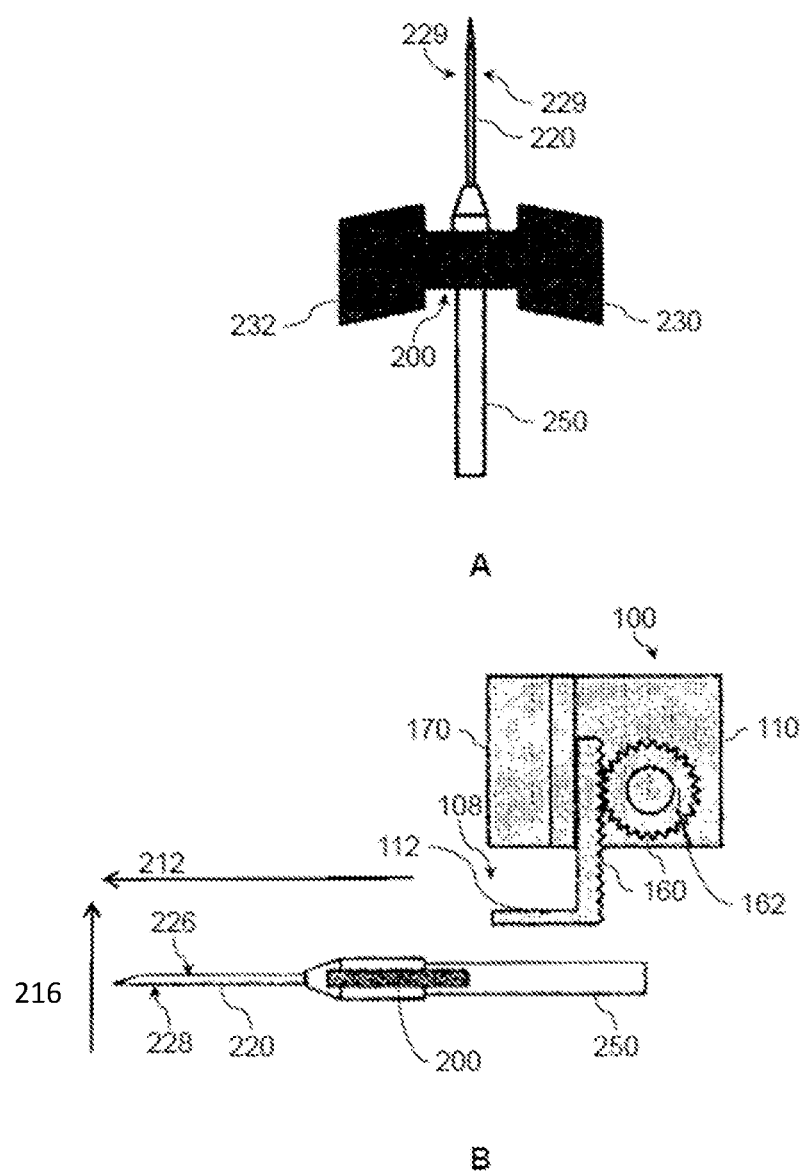
FIGS. 3A and 3B depict a further example embodiment of the inventive cannula holder as well as a further example embodiment of the inventive gripper apparatus for gripping said cannula holder. Insofar as technically feasible and not specified otherwise, the arrangements, forms, variants and advantages of this example embodiment correspond in particular to those from the preceding figures.

FIG. 3A depicts the cannula holder 200 in a view from above. The cannula holder 200 is fluidly connected to a cannula 220 and a tube 250. Preferably, regions 230, 232 are formed as wings, each extending outward from a respective longitudinal side 229 of the cannula 220.

FIG. 3B shows a sectional view through the gripper apparatus 100 in the receiving state for the cannula holder from FIG. 3A and together with same in a side view. FIG. 3B further depicts the longitudinal axis 214 of the cannula 200, the upper side 226 as well as the underside 228 of the cannula 220, and a vertical axis 216 of the cannula 220, wherein the vertical axis 216 extends from the underside 228 toward the upper side 226.

The gripper apparatus 100 comprises a first gripper element 110 and a second gripper element 112. At least in the receiving state depicted here, the gripper apparatus 100 exhibits an receiving area 108 situated between the first gripper element 110 and the second gripper element 112. The gripper apparatus 100 furthermore comprises a moving device 160 and a connecting device 170. The moving device 160 is thereby configured to move the second gripper element 112 relative to the first gripper element 110 and relative to the connecting device 170. Preferably, the first gripper element 110 is designed as a housing which accommodates the moving device 160 and is rigidly connected to the connecting device 170 and/or likewise accommodates same.

To move the second gripper element 112, the moving device 160 preferably comprises a gear and a rack, wherein the rack transforms a rotational movement of the gearwheel into a linear movement and thus moves the second gripper element 112 toward the first gripper element 110 and/or along the vertical axis 216 to bring it into the gripping state. The gripper apparatus 100, in particular the moving device 160, comprises an electric drive for said rotation, preferably an electric motor, in particular a stepper motor.

Preferably, the second gripper element 112 is shaped like a fork and comprises two grip regions 132, whereby particularly one of the grip regions is arranged at a longitudinal side of the cannula and the other one of the grip regions is arranged at the opposite longitudinal side of the cannula such that an area between these two grip regions, in particular at the underside of the cannula, remains free.

Preferably at least in the gripping state, the first gripper element 110 is arranged in an upper area above the upper side 226 and the second gripper element 212 in a lower area below the underside 228. The gripper element 110, which comprises further components of the gripper apparatus, is thereby advantageously arranged above the cannula and thus further away from a patient while the second gripper element 112 is arranged below the cannula and/or, depending on the cannula holder 200 form, alongside the cannula, wherein this is of smaller spatial extension, particularly relative to vertical axis 216, and thus the area below the cannula remains at least substantially free.

Figure 4:
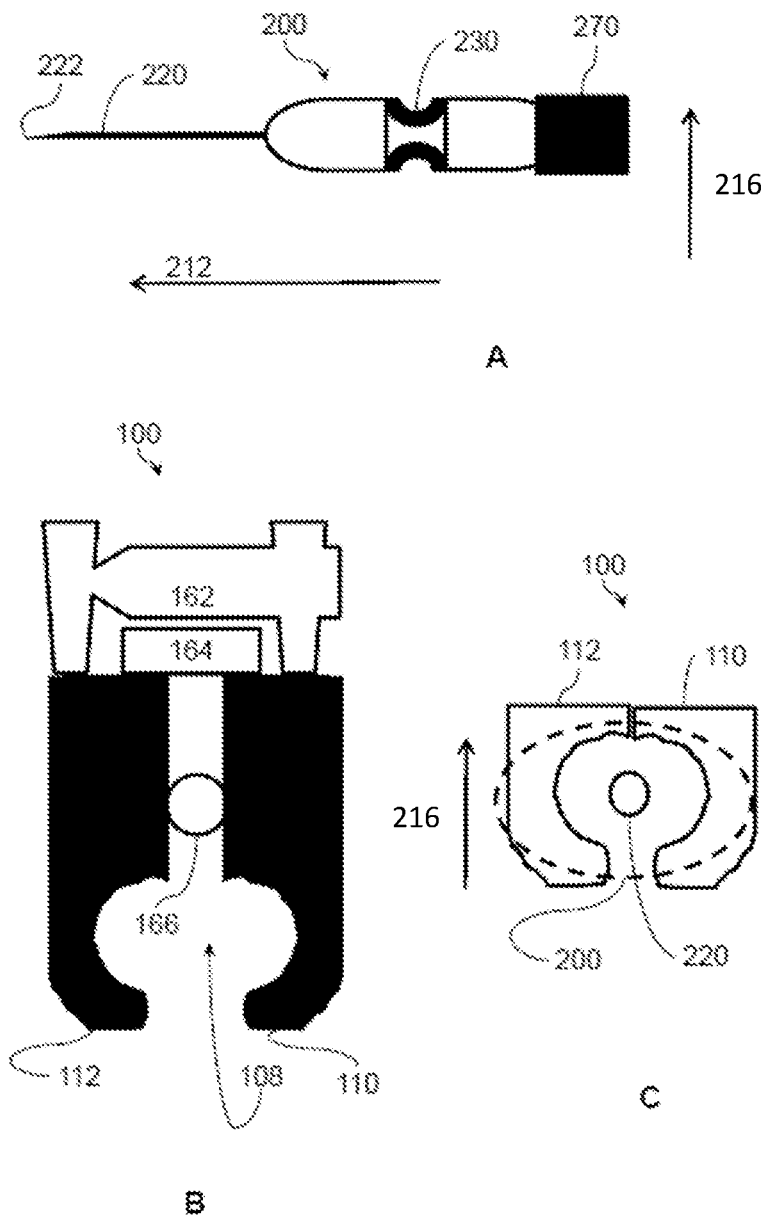

FIGS. 4A to 4C depict a further example embodiment of the inventive cannula holder as well as a further example embodiment of the inventive gripper apparatus for gripping the cannula holder. Insofar as technically feasible and not specified otherwise, the arrangements, forms, variants and advantages of this example embodiment correspond in particular to those from the preceding figures.

FIG. 4A shows a side view of a cannula with cannula holder 200. The cannula 220 exhibits a distal end 222, which defines a longitudinal axis 212 of the cannula, and is connected at the proximal end, situated opposite from distal end 222, to the cannula holder 200. The figure also depicts a vertical axis 216 pointing from the underside of the cannula to its upper side.

The cannula holder 200 moreover comprises a region 230 for gripping by means of the gripper apparatus and a connector part 270 for connecting to a tube, in particular an infusion tube. The cannula holder 200 thereby creates a preferably fluid connection between a lumen of the cannula 220 and a lumen of the tube.

Preferably, the cannula holder is cylindrically formed along the longitudinal axis 212. Alternatively and preferentially, the cannula holder 200 exhibits a rotational symmetry relative to the longitudinal axis 212 and is in particular oval. In particular, the cannula holder 200 can also not exhibit rotational symmetry relative to the longitudinal axis 212.

Preferably, the cannula holder exhibits a smaller spatial extension in the direction of the vertical axis 216. This can preferably be a height of at most 20 mm, further preferentially of at most 10 mm, and still further preferentially no more than 4 mm. The region 230 is thereby preferably formed as an indentation and/or at least not arranged at the underside such that said region 230 does not cause any additional spatial extension toward the vertical axis 216, in particular toward the underside.

FIG. 4B depicts the gripper apparatus 100 in a frontal view. The gripper apparatus 100 comprises a receiving area 108, a first gripper element 110 and a second gripper element 112, wherein the receiving area 108 is arranged between the two gripper elements 110, 112. The gripper elements 110, 112 are rotatably mounted about an axis of rotation in the direction of longitudinal axis 212 relative to each other by means of a bearing element. In particular, the gripper apparatus 100 is of pincer-like configuration, wherein the two gripper elements 110, 112 form the two limbs of the pincer.

The moving device comprises an actuator 162, in particular an electric actuator, for opening the gripper apparatus 100; i.e. for bringing the gripper apparatus 100 into a receiving state. Preferably, the actuator 162 is also designed to close the gripper apparatus 100; i.e. bring it into a gripping state. In so doing, the gripper elements 110, 112 rotate about the rotational axis relative to each other. Also preferably and alternatively or additionally, the moving device comprises a spring element 164 for closing the gripper apparatus. The spring element 164 can moreover be configured to keep the gripper apparatus 100 in the gripping state. Alternatively or additionally and preferentially, the grip regions of the gripper elements 110, 112 and the corresponding regions of the cannula holder can be formed so as to engage into one another in the gripping state and thus maintain the gripping state. One advantage of maintaining the gripping state by means of the spring element 164 and/or by means of the engaging can in particular be the gripping state being advantageously maintained passively.

FIG. 4c depicts a detail of the gripper apparatus 100 from FIG. 4B in the gripping state together with the cannula holder 200 from FIG. 4A from the front, wherein the gripper apparatus 100 grips the cannula 220 by the cannula holder 200 and by means of the first gripper element 110 and the second gripper element 112.

As particularly visible from the figure, the gripper apparatus 100 does not extend, at least substantially, below the cannula or cannula holder respectively and thus a lower area below the cannula/cannula holder remains free, whereby in particular a particularly flat angle is enabled for the insertion and/or securing of the cannula 220.

Furthermore, the connector part 270, as FIG. 4a depicts, is preferably arranged such that an attached tube extends in the connecting area along the longitudinal axis 212 and thus, together with the smaller spatial extension of the cannula holder 200 toward the vertical axis 216, in particular toward the lower area, lies flat against the patient and can in particular be secured by means of an adhesive strip. This advantageously enables the treatment safety, the treatment quality and/or the patient's comfort to be increased.

FIGS. 5A to 5D depict a further example embodiment of the inventive cannula holder as well as a further example embodiment of the inventive gripper apparatus for gripping said cannula holder. Insofar as technically feasible and not specified otherwise, the arrangements, forms, variants and advantages of this example embodiment correspond in particular to those from the preceding figures. Moreover, the gripper apparatus and/or the cannula holder can comprise further components which are not depicted in these figures for the sake of clarity but in particular constitute an integral part of the gripper apparatus or cannula holder respectively according to the invention.

Figure 5:
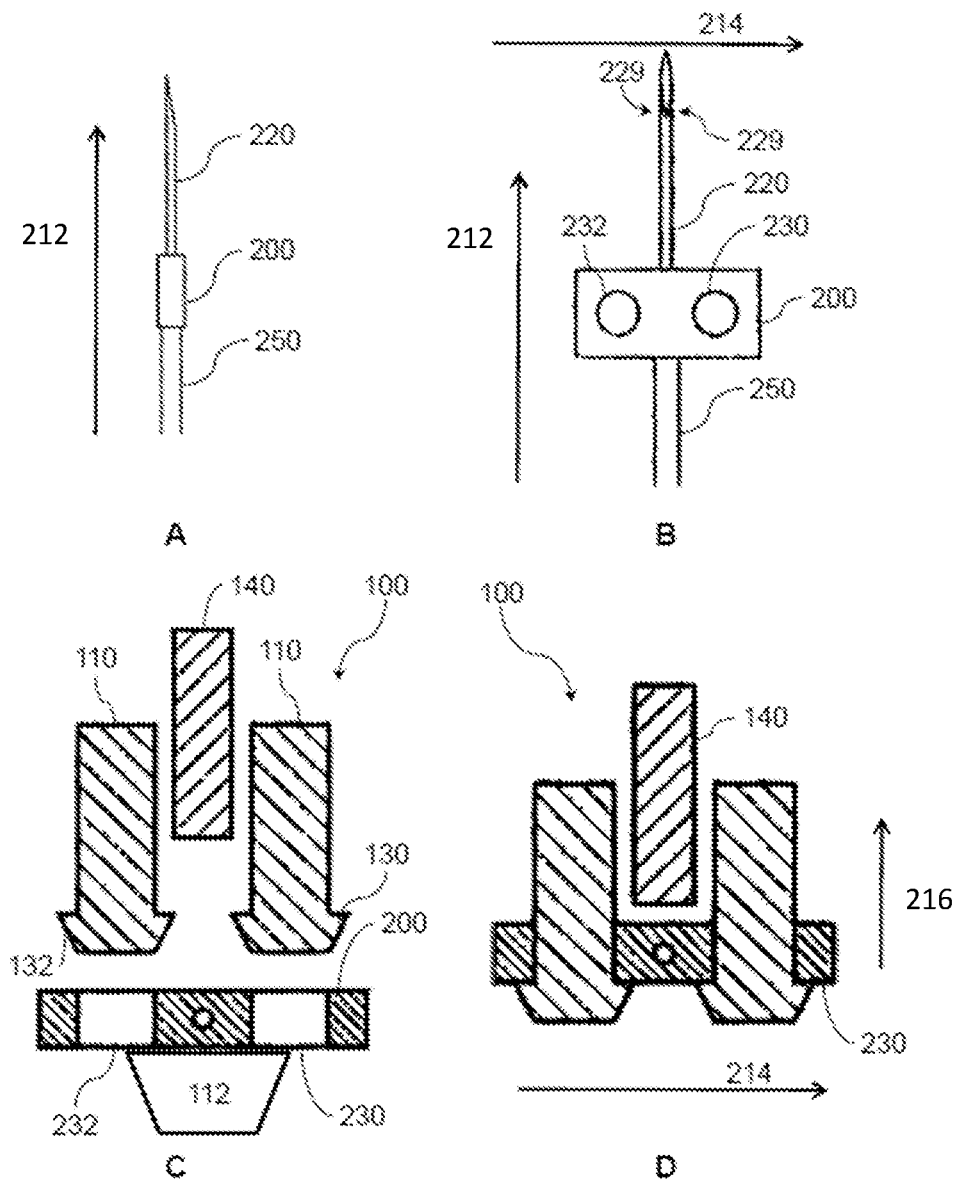

FIG. 5A shows the cannula holder 200 together with a cannula 220 and a tube 250 in a side view; also depicted is the longitudinal axis 212 of the cannula 220. The cannula holder 200 is integrally connected to the cannula 220, whereby the lumen of the cannula 220 is fluidly connected to a lumen of the cannula holder 200 and the cannula holder 200 is designed to be mechanically connected to the tube 250 in such a way as to establish a fluid connection between the tube 250, in particular a lumen of the tube, and the lumen of the cannula.

As is particularly discernible in the FIG. 5B view from above, the cannula holder 200 has two regions 230, 232 designed as engaging elements, in particular as receiving bores. These engaging elements 230, 232 of the cannula holder 200 correspond to engaging elements of the gripper apparatus 100.

Preferably, the engaging elements 230, 232 are arranged on a first and a second of the longitudinal sides 229 of the cannula 220 and formed in corresponding sides of the cannula holder 200. In so doing, the engaging elements are in particular arranged along a transverse axis 214 which extends from the first longitudinal side 229 toward the second longitudinal side 229. One advantage of this arrangement can in particular be that a rotation about a vertical axis; i.e. an axis pointing out of the drawing plane in FIG. 5B, is also prevented by a circular engaging element around said axis and/or a rotation about said vertical axis as well as longitudinal axis 212 is prevented or hindered since the greater spatial extension along the transverse axis 214 is leverage against rotation.

Alternatively, the cannula holder 200 can also exhibit only one such engaging element or, alternatively, at least three engaging elements. Preferably, when the cannula holder 200 comprises at least three engaging elements, these engaging elements are arranged along two axes, whereby in particular a rotation about all of the three spatial axes—even in the case of circular engaging elements—can be prevented. In particular, the gripper apparatus 100 thereby comprises a corresponding number as well as arrangement of engaging elements.

FIG. 5C depicts a sectional view through the gripper apparatus 100 in the receiving state as well as through the cannula holder 200. Thereby depicted in particular are two first gripper elements 110 and a second gripper element 112, the grip regions 130, 132 of the two first gripper elements 110 as well as an ejector element 140, while further components of the gripper apparatus 100—for instance a moving device—are not depicted for the sake of clarity. FIG. 5D shows a sectional view through the gripper apparatus 100 in the gripping state as well as through the cannula holder 200.

Each of the two first gripper elements 110 exhibit a respective grip region 130/132, whereby grip region 130 is formed as an engaging element which corresponds to the engaging element 230 of the cannula holder 200 and as a corresponding engaging element to the engaging element 232 corresponding to grip region 132.

The second of the gripper elements 112 is arranged with respect to the two first gripper elements 110 such that when the two first gripper elements 110 are moved by the moving device toward the cannula holder 200 in order to grasp it—i.e. to engage the engaging elements 130, 132 of gripper apparatus 100 into the engaging elements 230, 232 of the cannula holder 200—the second gripper element 112 supports the cannula holder 200 and the second gripper element 112 thereby effects an opposing force to counteract the engaging force. The first gripper elements 110 thereby preferably move along the vertical axis 216.

Preferably, the moving device of the gripper apparatus is designed to dislodge the second gripper element 112 from the cannula holder 200 after engagement, whereby in particular the spatial extension of the gripper apparatus can be reduced in the area of the cannula holder and/or the cannula, in particular in an area below the underside of the cannula.

Preferably, the gripper apparatus 100 comprises an ejector element 140 which is able to be moved by means of the moving device toward the cannula holder 200 at least in the gripping state in order to dislodge the engaging elements 130, 132 of the gripper apparatus 100 from the engaging elements 230, 232 of the cannula holder 200 and thus disengage the gripping state. Preferably, as illustrated in particular by the arrow in FIG. 6A, the ejector element 140 is thereby moved along the vertical axis 216 relative to the cannula holder and onto the cannula holder.

Figure 6:
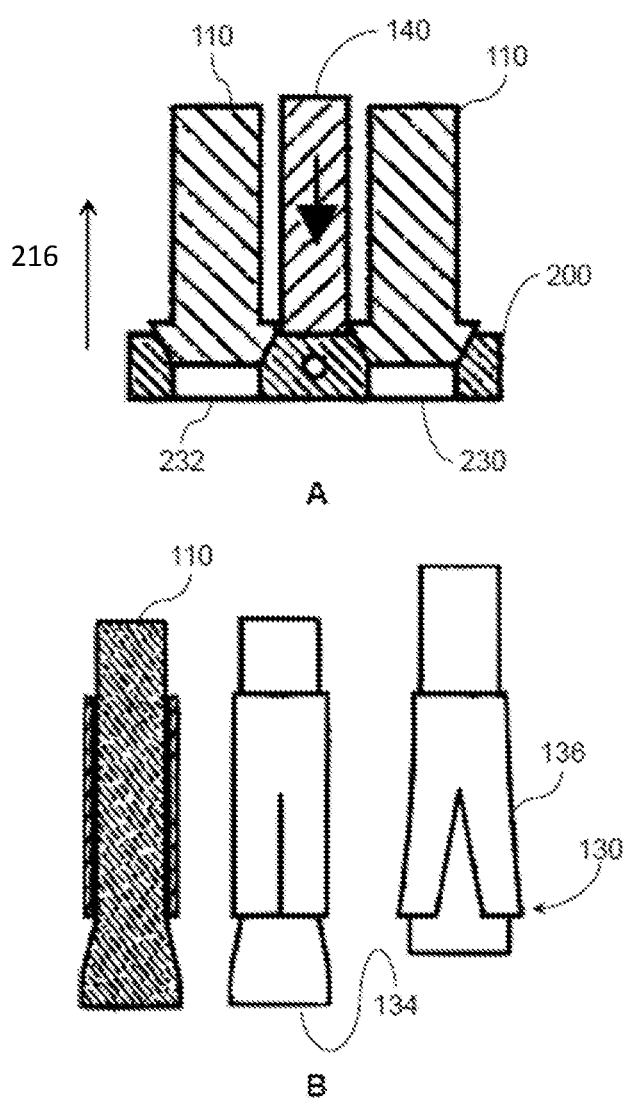

Also preferentially and alternatively or additionally to the ejector element 140, one or more, in particular all, of the first gripper elements 110 can be designed as expanding cylinders. Such an expanding cylinder 110 is depicted in FIG. 6B in sectional view and in side view—once in the closed state and once in the expanded state. The expanding cylinder 110 thereby has a base 134 at grip region 130 and is covered there. The gripper apparatus 100, in particular the expanding cylinder 110, furthermore comprises an expansion sleeve 136. Moreover, to bring the gripper apparatus 100 into the gripping state, the moving device is designed to push the expansion sleeve 136 toward and at least partially over the base 134 so that its circumference enlarges at grip region 130 and can in particular establish a form-fit connection with a corresponding engaging element or a corresponding receiving bore of the cannula holder. To disengage the gripping state, the expansion sleeve 136 is pushed in the opposite direction and the circumference thus diminished.

FIGS. 7A to 7D depict a further example embodiment of the inventive cannula holder as well as a further example embodiment of the inventive gripper apparatus for gripping said cannula holder. Insofar as technically feasible and not specified otherwise, the arrangements, forms, variants and advantages of this example embodiment correspond in particular to those from the preceding figures. Moreover, the gripper apparatus and/or the cannula holder can comprise further components which are not depicted in these figures for the sake of clarity but in particular constitute an integral part of the gripper apparatus or cannula holder respectively according to the invention.

Figure 7:
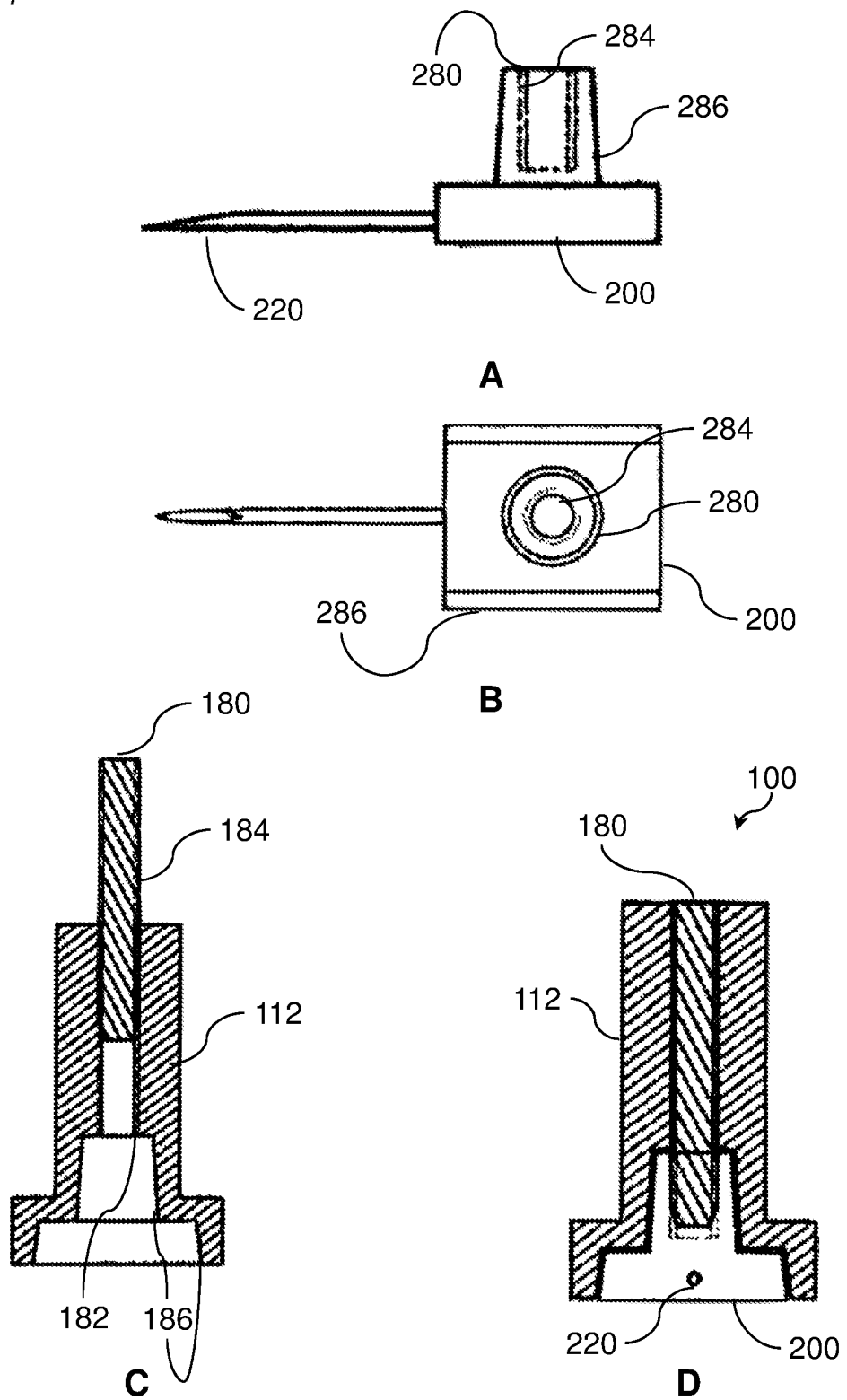

FIG. 7A shows the cannula holder 200 together with a cannula 220 in a side view. The cannula holder 200 comprises a threaded plug 280 having an internal thread 284. The threaded plug 280 is preferably configured as an upwardly tapering cone and its outer circumference accordingly exhibits a centering taper 286.

As is particularly discernible in the FIG. 7B view from above, the surface area of the cannula holder 200 is preferably of rectangular shape and the threaded plug 280 is preferably centrically arranged. Furthermore, the preferably rectangular outer contour of the cannula holder 200 comprises one or more, in particular two as depicted, lateral centering tapers 286. Said centering tapers enable the cannula holder to be centered relative to the gripper apparatus and in particular enable the non-circular lateral centering tapers 286 to prevent rotation about an axis of the threaded plug. FIG. 7B depicts the threaded plug 280 in partial section so that the internal thread 284 is visible.

FIG. 7C depicts a frontal view through the gripper apparatus 100 in the receiving state as well as through the cannula holder 200. In particular thereby shown is a first of the gripper elements, designed as spindle 180, and a second of the gripper elements 112, while further components of the gripper apparatus 100—for instance a moving device—are not depicted for the sake of clarity.

FIG. 7D depicts a frontal sectional view through the gripper apparatus 100 as well as through the cannula holder 200, whereby the gripper apparatus 100 is in the gripping state and grips the cannula holder 200. In this representation, the longitudinal axis of the cannula 220 in particular points out of the drawing plane.

The spindle 180 exhibits an external thread 184 which corresponds to the internal thread 284 of the cannula holder 200. Furthermore, the second gripper element 112 exhibits an internal thread 182 which corresponds to the external thread 184 so that the spindle can be screwed to the internal thread 182 of the second gripper element 112 as well as to the internal thread 284 of the cannula holder 200 by means of the external thread 184. In particular, to bring the gripper apparatus 100 into the gripping state, the moving device of the gripper apparatus 100 is designed to screw the spindle 180 to threaded plug 280.

Preferably, the second gripper element 112 exhibits one or more centering tapers 186 which correspond to the centering tapers 286 of the cannula holder.

Preferably, the gripper apparatus 100 comprises a further gripper element and/or a supporting element and/or a cannulation robot comprises a supporting element which is designed to support the cannula holder 200 when the spindle 180 is being screwed in.

Figure 8:
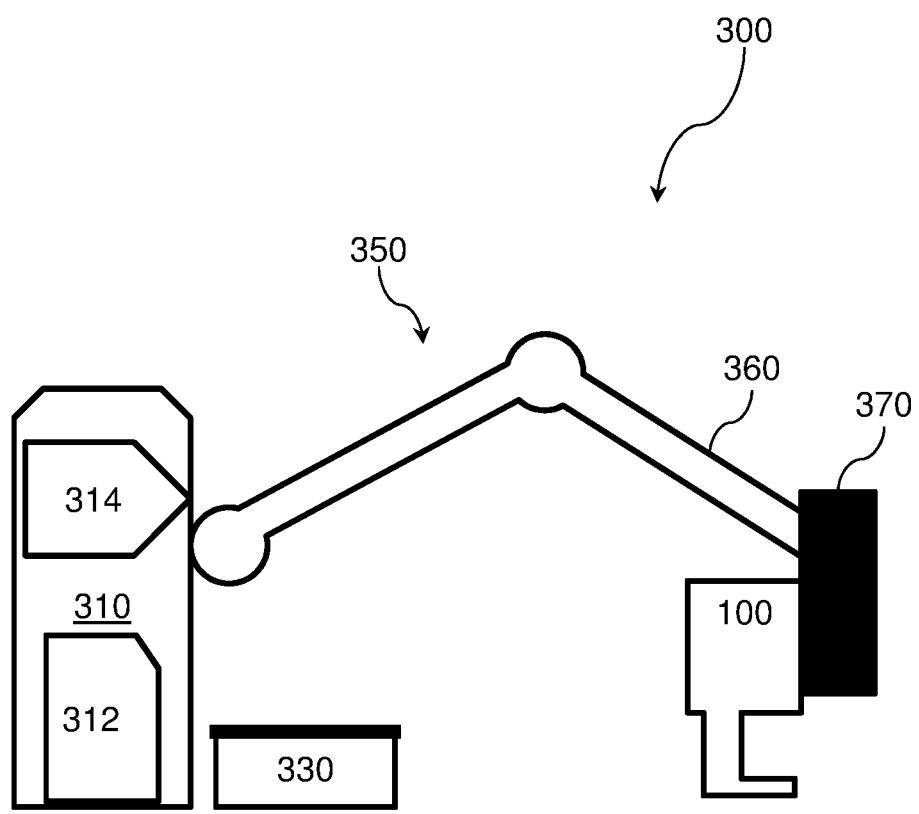

FIG. 8 depicts an embodiment of the cannulation robot according to the invention.

The cannulation robot 300 comprises a central system 310 which accommodates a plurality of cannulation robot components in one common housing and/or provides a stable base for further components of the cannulation robot. A tool arm device 350 is thus affixed to the central system of the cannulation robot, whereby the spatial position of said tool arm device 350 is predefined at least in regard to its fixation region on the central system 310. The tool arm device 350 comprises a tool arm 360 having articulated joints which is connected at one end to the central system 310 and at the other end has a connecting device 370 which is configured to connect to a tool device, a tool head.

Such a tool head can in particular be an embodiment of the inventive gripper apparatus. As illustrated, such a gripper apparatus 100 is mechanically connected, in particular form-fit and/or force-fit, to the connecting device 370. The cannulation robot 300 is thereby designed to move the gripper apparatus 100 toward the patient's body parts by means of the tool arm device 350 such that a blood vessel of said body part can be cannulated by means of a cannula gripped by the gripper apparatus 100.

Preferably, the cannulation robot 300 comprises a storage device 330 designed to store cannula holders, cannulas and/or cannulas with cannula holders. The cannulation robot 300 is thereby preferably designed for a cannula with cannula holder to be removed out of the storage device 330 by being grasped by the gripper apparatus 100.

To control in particular the tool arm device 350 and/or the gripper apparatus 100, the central system 310 preferably comprises a control apparatus 314 which is data-linked to a data processing apparatus 312 of the central system 310. In particular, the data processing apparatus 312 is thereto designed to determine control parameters for program-controlled cannulation. Additionally, the control apparatus 314 is preferably designed to transform these control parameters into control signals and output them for the control, in particular for the tool arm device 350 and/or the gripper apparatus 100.

Figure 9:
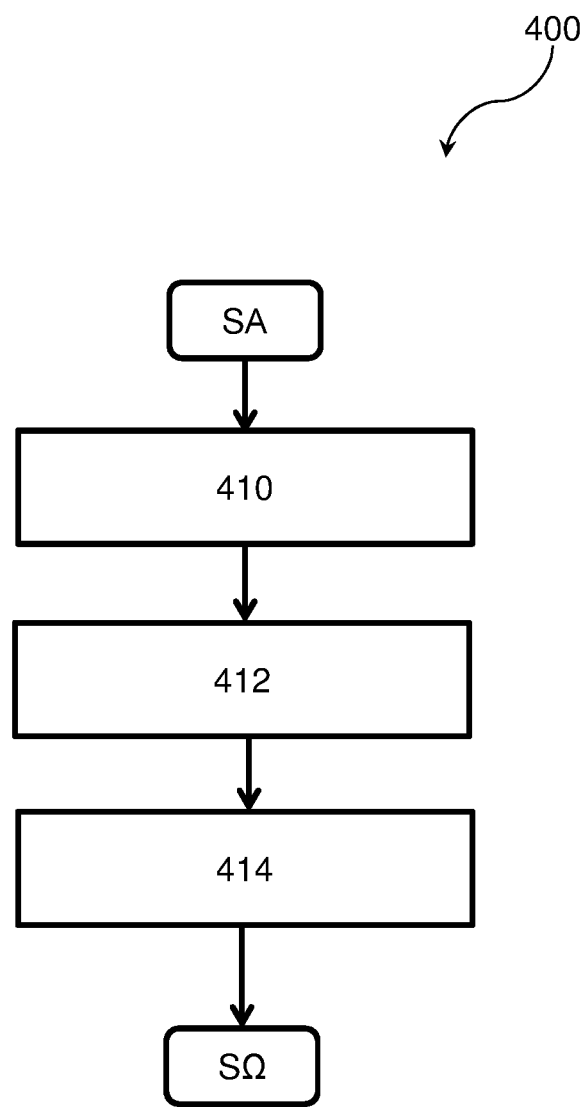

FIG. 9 depicts an example embodiment of the method according to the invention for the automated gripping of a cannula.

The method 400 comprises method steps 310, 312, 314. The method 400 begins at process start SA and ends at process end SΩ, whereby one or more method steps, in particular a sequence of method steps, and preferably the entire method, can be repeated.

In method step 410, a cannula with a cannula holder is provided or, alternatively, a cannula without a cannula holder is first provided and then connected to a likewise provided cannula holder.

In method step 412, the cannula holder, which is connected to the cannula, is disposed in a receiving area of a gripper apparatus.

Lastly, in method step 414, at least two gripper elements of the gripper apparatus are moved relative to each other and at least one of the gripper elements moved relative to the cannula holder until at least one of the gripper elements engages with the cannula holder.

FIGS. 10A to 10C depicts an example embodiment of the inventive cannulation robot as well as an example embodiment of the inventive cannula holder and illustrate an example embodiment of the inventive method for the automated gripping of a cannula by way of the plurality of method steps. Insofar as technically feasible and not specified otherwise, the arrangements, forms, variants, method steps and advantages of this example embodiment correspond in particular to those from the preceding figures. Moreover, the present embodiment can comprise further components which are not depicted in these figures for the sake of clarity but in particular constitute an inventive integral part thereof.

The cannulation robot 300 is in particular the cannulation robot from FIG. 8 and preferably comprises a gripper apparatus 100 according to the example embodiment from FIGS. 3A and 3B together with a corresponding cannula holder 200. The gripper apparatus 100 comprises a connecting device 170 which is affixed to a tool arm 360 of the cannulation robot by means of a connecting device 370 of the cannulation robot 300; i.e. is in particular mechanically connected to same.

FIG. 10A depicts the tool arm 360 and the connecting device 370 and a supporting element 332 of the cannulation robot as well as the cannula holder 200, which is connected to a cannula 220, in addition to the first gripper element 110, the second gripper element 112 and the connecting device 170 of the gripper apparatus 100. Thereby illustrated is a first method step of the method in which the cannula with cannula holder is provided. The cannula 220 is supported on the cannula holder 200 by supporting element 332. In particular, the supporting element 332 can be a component part of a storage device of the cannulation robot 300. The gripper apparatus 100 is furthermore in a receiving state in this method step and exhibits a receiving area 108 between the first gripper element 110 and the second gripper element 112.

FIG. 10B illustrates a further method step in which the cannula 220, i.e. in particular the cannula holder 200, is disposed in the receiving area 108. To that end, the tool arm 360 first drives the gripper apparatus 100 downward and then to the left relative to the drawing plane. In particular, the gripper apparatus is thereby first moved relative to the cannula holder 220 along; i.e. in particular against, a vertical axis 216 of the cannula, and then along a longitudinal axis 212 of the cannula, in particular toward the distal end of the cannula, until the cannula holder 200 or at least a part thereof is disposed in the receiving area 108. In particular, the second gripper element 112 is thereby disposed in a lower area below the underside of the cannula and is preferably of fork-like form with grip regions so that the two grip regions of the cannula holder 200 are each respectively disposed at a region alongside one of longitudinal sides of the cannula. This advantageously enables the supporting element 332 to support the cannula holder 200 while the cannula holder is being and/or is disposed in the receiving area 108.

Lastly, FIG. 10C illustrates yet a further method step of the method in which the gripper apparatus 100 is brought into a gripping state and the gripper elements 110,112 engage with the cannula holder 200. To that end, as suggested by the arrows in the figure, a moving device of the gripper apparatus 100 preferably effects a rotation of a gearwheel, in particular by means of an electric motor, which is converted into a linear movement of the second gripper elements 112 relative to the first gripper elements 110 by means of a rack. Doing so reduces the distance between the two gripper elements and the receiving area in which the cannula holder 200 is arranged, thereby achieving the gripping state and the gripper elements 110, 112 engaging with the cannula holder—in particular the grip regions of the gripper elements engaging with regions of the cannula holder corresponding to the grip regions of the gripper elements.

While the preceding describes at least one preferential embodiment, it will be noted that there is a great number of variations thereof. It is also to be noted that the embodiments described only represent non-limiting examples and are not thereby intended to limit the scope, the applicability or the configuration of the systems, apparatus and methods described herein. Rather, the foregoing description will provide a person skilled in the art with guidance for implementing at least one embodiment, wherein it is to be understood that a variety of changes can be made to the functioning and arrangement of the elements described in a preferential embodiment without thereby departing from the subject matter respectively set forth in the accompanying claims nor from legal equivalents thereof.

LIST OF REFERENCE NUMERALS 100 gripper apparatus
108 receiving area of gripper apparatus
110, 112 gripper element of gripper apparatus
114, 116 far side of gripper element 110/112
118 side of gripper element 110/112 facing the receiving area
120 cavity of respective gripper element
126 upper side of respective gripper element
128 receiving side, in particular underside, of respective gripper element
130, 132 grip region of gripper apparatus, in particular of gripper element
134 base of gripper element 110
136 expansion sleeve
140 ejector element of gripper apparatus
160 moving device of gripper apparatus
162 electric drive
164 spring element
166 bearing element
170 connecting device of gripper apparatus
180 spindle
182 internal thread of gripper element 112
184 external thread of spindle 180
186 centering taper of gripper element 112
200 cannula holder
212 cannula longitudinal axis
214 cannula transverse axis
216 cannula vertical axis
220 cannula
222 cannula distal end
224 cannula proximal end
226 cannula upper side
228 cannula underside
229 cannula longitudinal side
230, 232 region of cannula holder corresponding to grip region of gripper apparatus
240 connecting area of cannula holder for connecting to a cannula
242 cannula holder middle section
250 tube, in particular infusion tube
270 connector part for connecting to the tube
280 threaded plug
284 internal thread of cannula holder
286 centering taper of cannula holder
300 cannulation robot
310 cannulation robot central system
312 data processing apparatus
314 control apparatus
330 storage device for cannulas with cannula holders
332 supporting element for cannulas with cannula holders
350 tool arm device
360 tool arm of cannulation robot
370 cannulation robot connecting device for connecting to a tool head
400 method for the automated gripping of a cannula
SA process start
SΩ process end
410 to 414 method steps

The invention claimed is:

1. A gripper apparatus for a cannulation robot for gripping a cannula holder, the gripper apparatus comprising two gripper elements and a moving device, wherein:
   the gripper apparatus is configured such that the two gripper elements are able to be moved relative to each other and work in concert with one another to grip a cannula holder;
   the moving device is configured to move the two gripper elements relative to one another and configured to move at least one of the gripper elements relative to a cannula holder when in use;
   the moving device is configured to bring the gripper apparatus into a gripping state for gripping whereby at least one of the gripper elements is engaged with a cannula holder;
   each of the two gripper elements has a respective grip region, and
   in the state, either (1) the gripper apparatus is oriented to be arranged in an upper area above an upper side of a cannula and facing away from a patient when a distal end of the cannula is inserted into a patient, or (2) the grip regions are arranged and the gripper elements are formed such that a lower area below an underside of a cannula and facing a patient when the distal end of the cannula is inserted into the patient, is substantially free, or (3) both (1) and (2).

2. The gripper apparatus according to claim 1, a cannula, and a cannula holder, wherein, at least in the gripping state, the cannula is held by the cannula holder and the gripper apparatus only contacts the cannula holder.

3. The gripper apparatus according to claim 1, a cannula, and a cannula holder, wherein, when the gripper elements are gripping, the moving device only moves in an area surrounding the cannula holder, an area surrounding the distal end of the cannula remains free of gripper elements, or the moving device only moves in an area surrounding the cannula holder and an area surrounding the distal end of the cannula remains free of gripper elements.

4. The gripper apparatus according to claim 1, a cannula, and a cannula holder, wherein:
   the gripper elements are arranged adjacent one another;
   each gripper element has a respective receiving side and a respective opposite side;
   each receiving side faces away from the respective opposite side;
   each gripper element has a cavity for at least partially receiving a cannula holder;
   the grip regions are formed in the respective receiving sides;
   each cavity extends from the respective receiving side toward the respective opposite side;
   the cannula holder comprises a middle section including two protrusions;
   the two protrusions are configured to be introduced into the respective cavities from the respective receiving sides of the two gripper elements in a receiving state of the gripper apparatus;
   the cannula holder has two counterpart grip regions that respectively correspond to the grip regions of the two gripper elements; and
   the moving device is designed, for the gripping of the cannula after the middle section of the cannula holder has been introduced into the cavity, to move the two gripper elements away from each other along the middle section and in each case in a direction toward the respective opposite side until at least the respective grip region form-fits and/or force-fits with the corresponding counterpart grip region of the cannula holder.

5. The gripper apparatus according to claim 1, a cannula, and a cannula holder, wherein:
   the gripper apparatus further comprises a receiving area for at least partially receiving the cannula holder;
   the gripper elements are arranged adjacent to the receiving area;
   each gripper element has a respective side facing the receiving area;
   at least one of the grip regions is formed on the respective facing side of the respective gripper element;
   the cannula holder has two counterpart grip regions that respectively correspond to the grip regions of the two gripper elements; and
   for the gripping of the cannula after the cannula holder has been arranged in the receiving area, the moving device is designed to move the gripper elements toward each other as well as move the at least one grip region formed on the respective facing side toward the corresponding counterpart grip region of the cannula holder until the at least one grip region formed on the respective facing side is form-fit and/or force-fit to the corresponding counterpart grip region.

6. The gripper apparatus, cannula, and cannula holder according to claim 5, wherein at least in the gripping state and during gripping:
   a first of the gripper elements is arranged on a first longitudinal side of the cannula;
   a second of the gripper elements is arranged on a second longitudinal side of the cannula opposite from the first longitudinal side; and
   a respective grip region is, in each case, formed on the facing side of the first and/or second gripper element.

7. The gripper apparatus, cannula, and cannula holder according to claim 6, wherein:
   the first gripper element and the second gripper element are each of pincer-like form; and
   the first and the second gripper element are rotatably mounted for rotation relative to one another about a rotational axis that is aligned with a direction of a longitudinal axis of the cannula.

8. A gripper apparatus for a cannulation robot for gripping a cannula with a cannula holder, comprising:
   two gripper elements able to be moved relative to each other and which work in concert to grip the cannula holder;
   a moving device which is configured to move the two gripper elements relative to each other and move at least one of the gripper elements relative to the cannula holder; and
   a receiving area for at least partially receiving the cannula holder; wherein
   the moving device can bring the gripper apparatus into a gripping state for gripping in which at least one of the gripper elements is engaged with the cannula holder,
   the gripper elements are arranged adjacent to the receiving area and each has a respective side facing the receiving area,
   at least one grip region is formed on the facing sides,
   for the gripping of the cannula after the cannula holder has been arranged in the receiving area, the moving device is designed to move the gripper elements toward each other as well as move the at least one grip region toward the corresponding region of the cannula holder relative to said cannula holder until at least the at least one grip region is form-fit and/or force-fit to the corresponding region, in the gripping state and during gripping,
- a first of the gripper elements is arranged on a first longitudinal side of the cannula,
- a second of the gripper elements is arranged on a second longitudinal side of the cannula opposite from the first longitudinal side, and
- a respective grip region is in each case formed on the facing side of the first and/or second gripper element, at least in the gripping state, a first of the gripper elements is arranged in an upper area above the upper side of the cannula and a second of the gripper elements is arranged in a lower area below an underside of the cannula, and the moving device is designed to move the second gripper element along a longitudinal axis of the cannula as well as toward the upper area.

9. The gripper apparatus according to claim 1, a cannula, and a cannula holder, the cannula holder having one or more engaging elements, wherein:
- one or both of the two gripper elements comprise grip regions formed as corresponding engaging elements that correspond to the one or more engaging elements of the cannula holder; and
- the gripper apparatus further comprises one or more second gripper elements that is/are arranged, in each case, with respect to a respective one of the two gripper elements such that when gripping the one or more second gripper elements support the cannula on or by means of the cannula holder and thereby effect an opposing force counteracting an engaging force.

10. A gripper apparatus for a cannula with a cannula holder having an internal thread, the gripper apparatus comprising:
- two gripper elements able to be moved relative to each other and which work in concert to grip the cannula holder; and
- a moving device which is configured to move the two gripper elements relative to each other and move at least one of the gripper elements relative to the cannula holder; wherein
- the moving device can bring the gripper apparatus into a gripping state for gripping in which at least one of the gripper elements is engaged with the cannula holder,
- a first gripper element comprises a spindle having an external thread which corresponds to the internal thread of the cannula holder;
- a second gripper element has an internal thread corresponding to the external thread of the spindle; and
- the moving device is designed to screw at least part of the spindle into the internal thread of the cannula holder.

\* \* \* \* \*